US008426368B2

(12) United States Patent  
Haley et al.

(10) Patent No.: US 8,426,368 B2  
(45) Date of Patent: Apr. 23, 2013

(54) METHOD OF AMELIORATING OXIDATIVE STRESS AND SUPPLEMENTING THE DIET

(75) Inventors: Boyd E. Haley, Nicholasville, KY (US); Niladrl Narayan Gupta, Georgetown, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 299 days.

(21) Appl. No.: 12/818,807

(22) Filed: Jun. 18, 2010

(65) Prior Publication Data

US 2011/0237525 A1    Sep. 29, 2011

Related U.S. Application Data

(63) Continuation-in-part of application No. 12/731,415, filed on Mar. 25, 2010.

(51) Int. Cl.
*A61K 38/05*    (2006.01)
*A61K 38/00*    (2006.01)

(52) U.S. Cl.
USPC .................................. 514/21.91; 514/1.1

(58) Field of Classification Search .................. None
See application file for complete search history.

(56) References Cited

U.S. PATENT DOCUMENTS

| | | | |
|---|---|---|---|
| 4,039,446 | A | 8/1977 | Ban et al. |
| 4,281,086 | A | 7/1981 | Gaul, Jr. et al. |
| 4,433,154 | A | 2/1984 | Hirai |
| 4,508,838 | A | 4/1985 | Buckl |
| 4,673,562 | A | 6/1987 | Davison et al. |
| 4,751,286 | A | 6/1988 | Packard et al. |
| 4,969,995 | A | 11/1990 | Jackson et al. |
| 5,073,575 | A | 12/1991 | Blanch et al. |
| 5,173,470 | A | 12/1992 | Bruening et al. |
| 5,200,473 | A | 4/1993 | Jeanneret-Gris |
| 5,494,935 | A | 2/1996 | Miller et al. |
| 5,615,862 | A | 4/1997 | Gaudette |
| 5,766,478 | A | 6/1998 | Smith et al. |
| 6,013,246 | A | 1/2000 | Langworth |
| 6,025,140 | A | 2/2000 | Langel et al. |
| 6,586,600 | B2 | 7/2003 | Atwood et al. |
| 6,852,369 | B1 | 2/2005 | Atwood |
| 6,936,729 | B2 | 8/2005 | Wolff et al. |
| 7,087,770 | B2 | 8/2006 | Wolff et al. |
| 7,417,034 | B2 | 8/2008 | Susilo |
| 7,482,160 | B2 | 1/2009 | Monahan et al. |
| 2002/0136763 | A1 | 9/2002 | Demopoulos et al. |
| 2004/0132101 | A1 | 7/2004 | Lazar et al. |
| 2006/0099239 | A1 | 5/2006 | Coleman et al. |
| 2006/0269488 | A1 | 11/2006 | Ott |
| 2007/0026109 | A1 | 2/2007 | Foulger |
| 2007/0077586 | A1 | 4/2007 | Baggot |
| 2007/0191281 | A1 | 8/2007 | Wolff et al. |

FOREIGN PATENT DOCUMENTS

EP    057797    8/1982

OTHER PUBLICATIONS

Gelinsky, M. et al., Tripodal Pseudopeptides with Three Histidine or Cysteine Donors: Synthesis and Zinc Complexation, Inorg. Chem. 2002, 41, 2560-2564 (Apr. 5, 2002).

Ludiow, F.R. et al., Two-Vial, LC-MS Identifiction of Ephedrine Receptors froma Solution-Phase Dynamic Combinatorial Library of over 9000 Components, J. Am. Chem. Soc. 2008, 130, 12218-12219 (Aug. 21, 2008).
West, K.R. et al., Dynamic Cominatorial Libraries of Disulfide Cages in Water, Organic Letters, 2005, 7(13), 2615-2618 (May 26, 2005) See Compound 5.
Wallen, E.A.A. et al., New Prolyl Oligopeptidase Inhibitors Developed from Dicarboxylic Acid Bis (L-prolyl-pyrrolidine) Amides, J. Med. Chem. 2003, 46. 4543-4551, (Sep. 4, 2003).
PCT/US2010/1050512 International Search Report dated Jun. 21, 2011.
PCT/US2010/050512 Written Opinion dated Jun. 21, 2011.
Uwe Schröder, Lothar Beyer, and Joachim Sieler; "Synthesis and X-ray structure of a new silver(I) coordination polymer assembled as one-dimensional chains";Inorganic Chemistry Communications; vol. 3, Issue 11, Nov. 2000, pp. 630-633.
Matthew M. Matlock, Brock S. Howerton and David A. Atwood; "Irreversible precipitation of mercury and lead"; Journal of Hazardous Materials; vol. 84, Issue 1, Jun. 1, 2001, pp. 73-82.
Matthew M. Matlock, Brock S. Howerton, Kevin R. Henke and David A. Atwood; "A pyridine-thiol ligand with multiple bonding sites for heavy metal precipitation"; Journal of Hazardous Materials; vol. 82, Issue 1, Mar. 19, 2001, pp. 55-63.
Paul Römkens, Lucas Bouwman, Jan Japenga and Cathrina Draaisma; "Potentials and drawbacks of chelate-enhanced phytoremediation of soils"; Environmental Pollution; vol. 116, Issue 1, Jan. 2002, pp. 109-121.
International Preliminary Report on Patentability for International Application No. PCT/US2010/050512 dated Apr. 3, 2012.
Tandon et al.; "Chelation in Metal Intoxication XXXVIII: Effect of Structurally Different Chelating Agents in Treatment of Nickel Intoxication in Rat"; Fundamental and Applied Toxicology, vol. 31, 141-148 (1996).
Anderson, Ole; "Principles and Recent Developments in Chelation Treatment of Metal Intoxication"; Chemical Reviews (1999) vol. 99, 2683-2710.
Non-Final Office Action for U.S. Appl. No. 12/630,259 dated Nov. 21, 2011.
Final Office Action for U.S. Appl. No. 12/630,259 dated Apr. 25, 2012.
Yamada et al.; "Solid-Phase Synthesis of Dehydroalanine Derivatives"; Tetrahedron Letters (1998), vol. 39, Issue 3-4, pp. 289-292.
Kudo et al.; "Efficient Synthesis of Macrocycles by Oxidation of Cysteine-Based Dithiols"; Tetrahedron Letters (2001), vol. 42, Issue 44, pp. 7847-7850.
Non-Final Office Action for U.S. Appl. No. 12/892,464 dated Feb. 2, 2012.
Non-Final Office Action for U.S. Appl. No. 12/731,415 dated May 24, 2012.

Primary Examiner — Marcela M Cordero Garcia
(74) Attorney, Agent, or Firm — King & Schickli, PLLC

(57) ABSTRACT

A method of supplementing a diet and ameliorating oxidative stress in a mammal includes administering a pharmaceutically effective amount of lipid soluble, hydrophobic active compounds having a chemical structure:

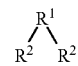

wherein $R^1$ is an aromatic backbone and $R^2$ is a sulfur containing ligand. Through formation of disulfide linkages other moieties can be attached to $R^2$ converting the hydrophobic base into a water soluble entity, for ease of delivery, which can be reconverted back to the original compound by biochemical reduction in the blood stream.

45 Claims, No Drawings

METHOD OF AMELIORATING OXIDATIVE STRESS AND SUPPLEMENTING THE DIET

This application is a continuation-in-part (CIP) of U.S. patent application Ser. No. 12/731,415 filed on 25 Mar. 2010, the full disclosure of which is incorporated herein by reference.

TECHNICAL FIELD

The present invention relates generally to the field of dietary supplements for mammals and, more particularly, to methods of supplementing a diet, removing heavy metals and other toxins and ameliorating oxidative stress.

BACKGROUND OF THE INVENTION

Heavy metals such as mercury, lead, cadmium and silver can bind to proteins on the proteins' incorporated cysteine residues which contain sulfhydryl or —SH groups. This abnormally inhibits or activates their biological properties. Further, a heavy metal binding specific proteins can induce damage that leads to overproduction or leakage of reactive oxygen species (ROSs) from their normal locations. These ROSs, mostly produced in the mitochondria of the cells of the body, then react with protein, nucleic acid (DNA, RNA) and lipid molecules in the healthy cell changing their property/chemistry and leading to unhealthy cells that may die or at least be unable to defend themselves from other stress factors such as viral infection. In addition to heavy metals there are many other chemical toxicants that can induce oxidative stress including, for example, radiation toxicity, acetominophen and dioxin. Further, it is well known that the oxidation of reduced glutathione (GSH) to oxidized glutathione (G-S—S-G) is one of the first biochemical signals for apoptotic cell death (or programmed cell death). The inadvertent oxidation of GSH by toxin produced ROSs could lead to increased GSSG and cell death also. In the healthy body GSH accomplishes protection against heavy metal toxicity, organic toxins and hydroxyl free radical damage due to its chemical ability to; (1) chelate heavy metals, (2) its use by the enzyme glutathione-S-transferase (GST) to produce GS-toxin complexes that are actively removed from the intracellular location into the blood and then actively removed from the blood by GS-toxin receptors in the bilary transport system of the liver and into the bile and feces and (3) GSH's ability to scavenge and eliminate hydroxyl free radicals.

It is well known that excess exposures to heavy metals, above the capacity of the normal cellular GSH capability to bind and remove, inhibit the enzymes involved in the synthesis of GSH and the recovery of oxidized GSH from GSSG (oxidized glutathione) leading to decreased GSH levels that are identified as oxidative stress. Also, such heavy metal excesses lead to an overproduction of free radicals by the mitochondrial and further oxidizes GSH to GSSG and decreases the cells ability to remove toxins (organic and heavy metals) by the lowering of the intracellular concentration of GSH. Therefore, an ideal way to recover GSH levels would be to develop a non-toxic compound with membrane penetrating abilities, heavy metal binding properties and reactive oxygen species scavenging properties that were superior to GSH.

With these properties a well designed compound with both heavy metal chelation properties and antioxidant properties could; (1) easily penetrate cell membranes and the blood brain barrier, (2) bind heavy metals preventing their inhibition of enzymes needed to synthesize GSH and recover GSH from GSSG, (3) decrease free radical formation by reversing heavy metal inhibition of the mitochondrial electron transport system, and (4) scavenge hydroxyl free radicals preventing oxidation of naturally produced GSH to GSSG. With these four properties such a compound could dramatically increase intracellular GSH and reduce free radical damage and allow the cells to recover to a normal state. In addition, the increase in intracellular GSH would allow GST to remove organic toxins built up during periods of toxicity and enhance the ability of the P-450 system to further detoxify the subject using the natural system. For example, it is well known that GSH is directly involved in binding to components of viral replication systems inhibiting viral replication. Low GSH levels are a major risk factor for several viral infections and high GSH seems involved in reversing and preventing such viral infections.

In order to medically prevent or reduce the oxidative stress problem identified as low GSH levels, heavy metals must be excreted by natural means or complexed by medically based chelator compounds that render them biologically unavailable to elicit their toxic effects. To effect this removal and tightly bind the heavy metals, the treating compound must be able to effectively remove the metal from the single sulfur residue and bind it more tightly than is capable with only one sulfur to metal bond. That is, the compound must make at least two intramolecular sulfur to metal bonds to be able to prevent subsequent reaction or exchange of the complexed metal with other biomolecules. This requires that the chelating molecule contain at least two sulfhydryls that are one extended arms that allow for extended freedom of rotation and movement of the sulfhydryls so that the most stable orientiation for binding the heavy metal can be obtained. For example, the ideal chelating compound must have degrees of freedom of rotation and movement of the sulfur bonds to be able to bind different heavy metals that have different coordination chemistries (e.g. different bond angles that confer tighter bonding). For example, $Hg^{2+}$ and $Pb^{2+}$ both can form two bonds with —SH groups, but the most stable binding of each metal would have different bond angles.

To be effective at treating both intracellular heavy metal toxicity and radiation toxicity as well as oxidative stress associated therewith, the treating compound has to be able to cross the cellular membrane with efficiency and, if the brain is involved, the treating compound must be able to cross the blood brain barrier. In order to be able to do this the compound has to be quite hydrophobic in nature in order to be able to pass through the lipid bilayer of the cell membrane to reach the site of heavy metal binding and intercept the ROS produced by the mitochondria before they react and damage cellular constituents. Further, the ideal treating compound must be of very low toxicity to cells and not disrupt membranes or biological pathways and it should not be involved in any natural metabolism that would destroy its physical character. In addition, the treating compound must be efficiently excreted from all tissues of the body in a non-toxic form. For example, if the treating compound binds mercury cation ($Hg^{2+}$) it must carry this metal ion out of the body and not distribute it to other organs such as the kidney.

The ideal treatment compound must also exhibit stability to air oxidation and breakdown so that the treating compound can be effectively stored and packaged for delivery to the patient in original, active form. The treating compound ideally must also be suited for ease of administration to a patient. Further, the treating compound must not deplete the body of essential metals such as zinc and copper. In addition, it should also have an adequately long plasma half-life such that it is possible to take eight hours rest and not have the treating compound significantly depleted from the plasma and tissues.

The present invention relates to methods of supplementing the diet of a mammal, removing heavy metals and other toxins from a mammal and ameliorating undesirable oxidative stress in a mammal using a single molecule with cell membrane penetrating abilities, metal chelation and oxygen radical scavenging properties, and non-toxic character. To aid in intraveneous delivery, some hydrophobic (lipophilic) compounds are made to be hydrophilic by formation of hydrophilic (water soluble) analogs via attachment by disulfide linkages that are converted after delivery by the body's reducing capability back to the hydrophobic state. Other compounds have the reverse ability in that they are delivered as hydrophobic esters and converted intracellular, by well known esterases, into water soluble, hydrophilic compounds that are more excretable through the kidneys.

SUMMARY OF THE INVENTION

In accordance with the purposes of the present invention as described herein, a method of supplementing a diet of a mammal is provided. That method comprises: administering to said mammal a pharmaceutically effective amount of a compound having a chemical formula:

where $R^1=$

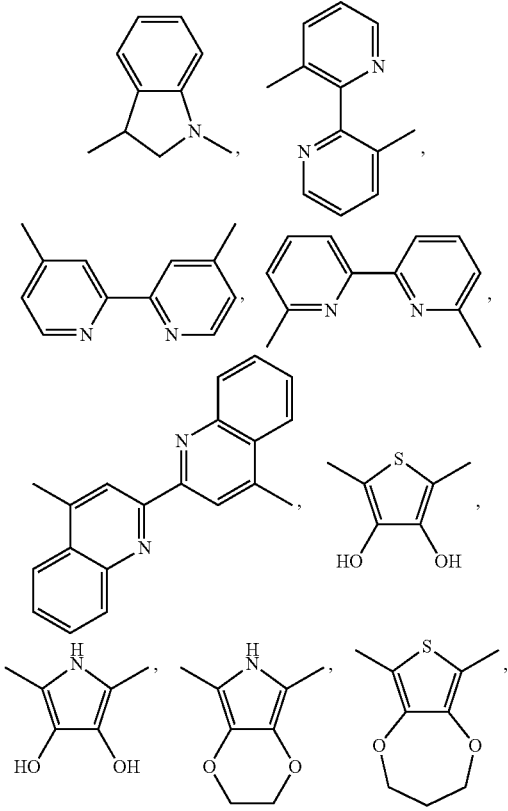

-continued

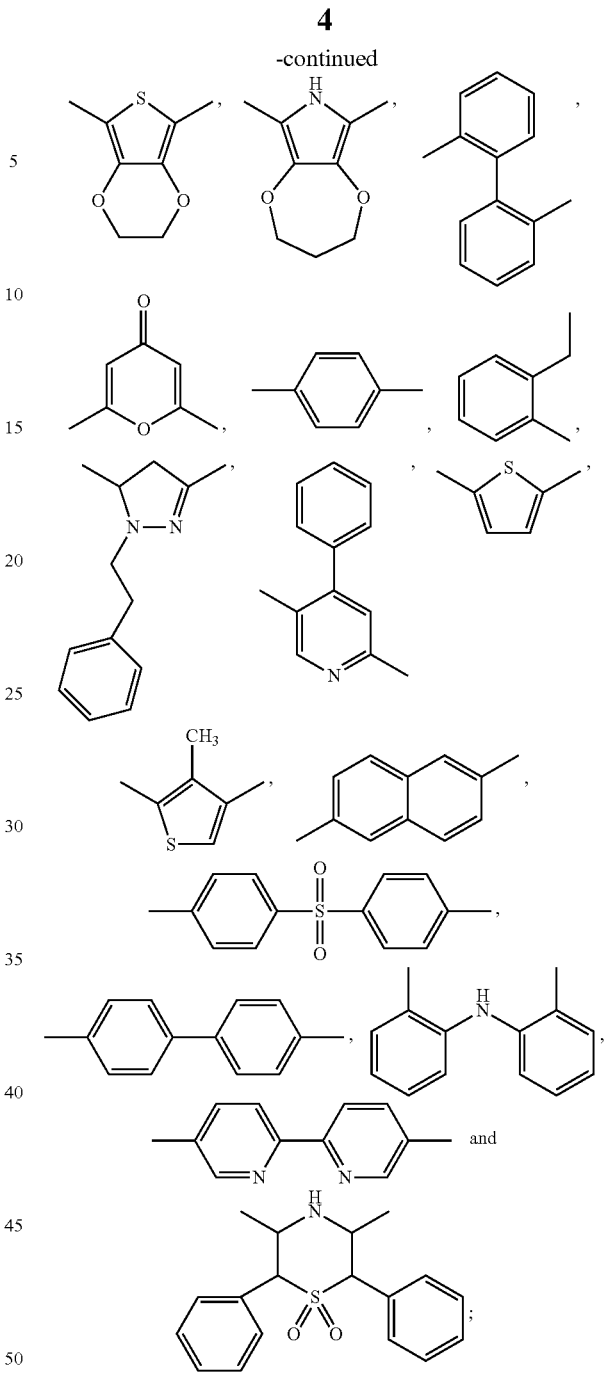

and
where $R^2=$

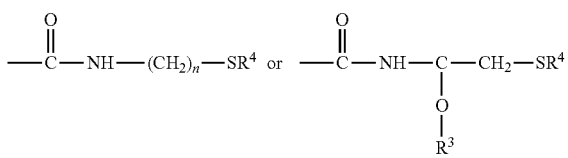

where $R^3=$ethyl or methyl, $R^4=$hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4. The $R^4$ attachment, other than hydrogen, converts the hydrophobic base compound to a hydrophilic, water soluble compound. The $R^3$ attachment makes the base compound susceptible to esterase conversion intracellular into a hydrophilic compound.

In accordance with yet another aspect of the present invention, a method to remove heavy metals and toxins from a mammal comprises: administering to said mammal a pharmaceutically effective amount of a compound having a chemical formula:

where $R^1$=

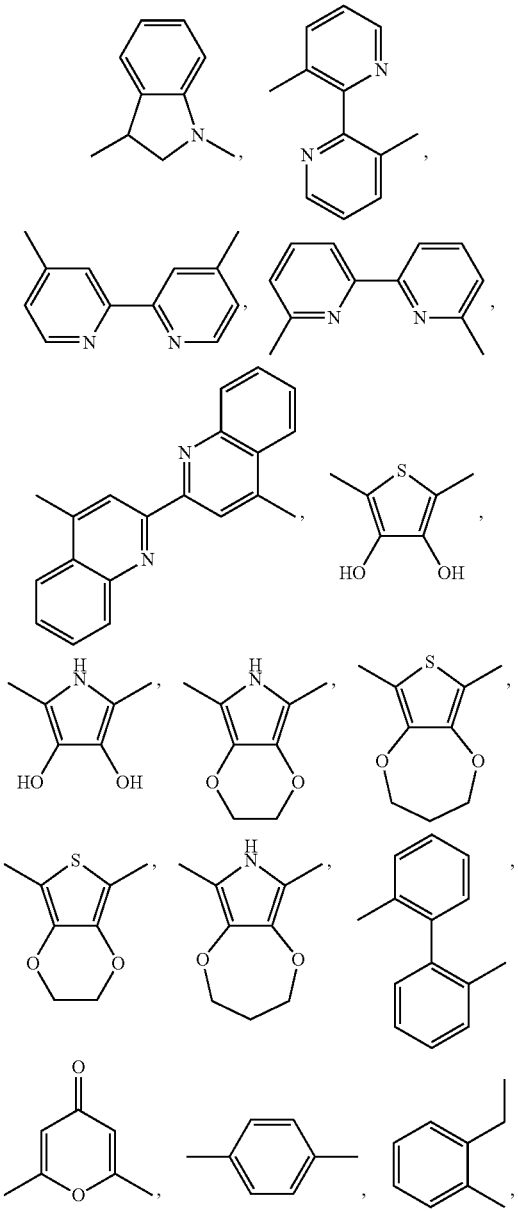

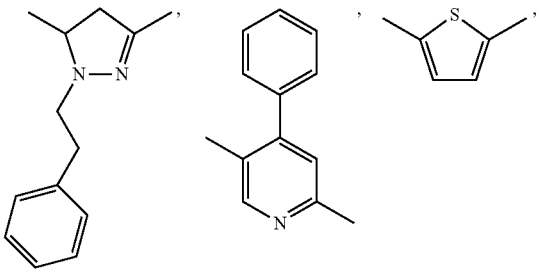

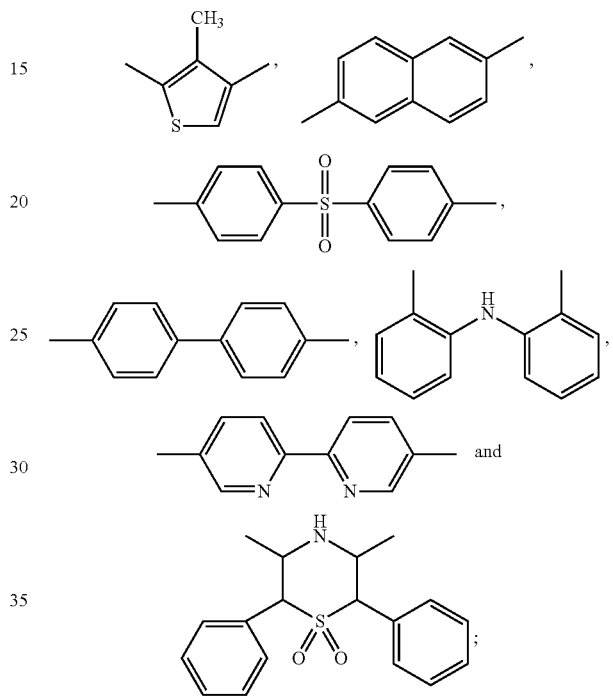

and
where $R^2$=

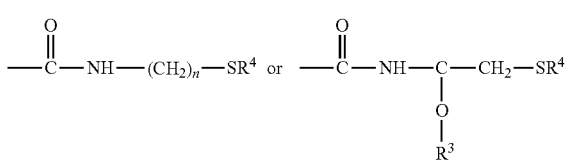

where $R^3$=ethyl or methyl, $R^4$=hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4. The $R^4$ attachment, other than hydrogen, converts the hydrophobic base compound to a hydrophilic, water soluble compound. The $R^3$ attachment makes the base compound susceptible to esterase conversion intracellular into a hydrophilic compound.

In accordance with yet another aspect of the present invention a method is provided for relieving oxidative stress in a mammal. That method comprises: administering to said mammal a pharmaceutically effective amount of a compound having a chemical formula:

where $R^1$ =

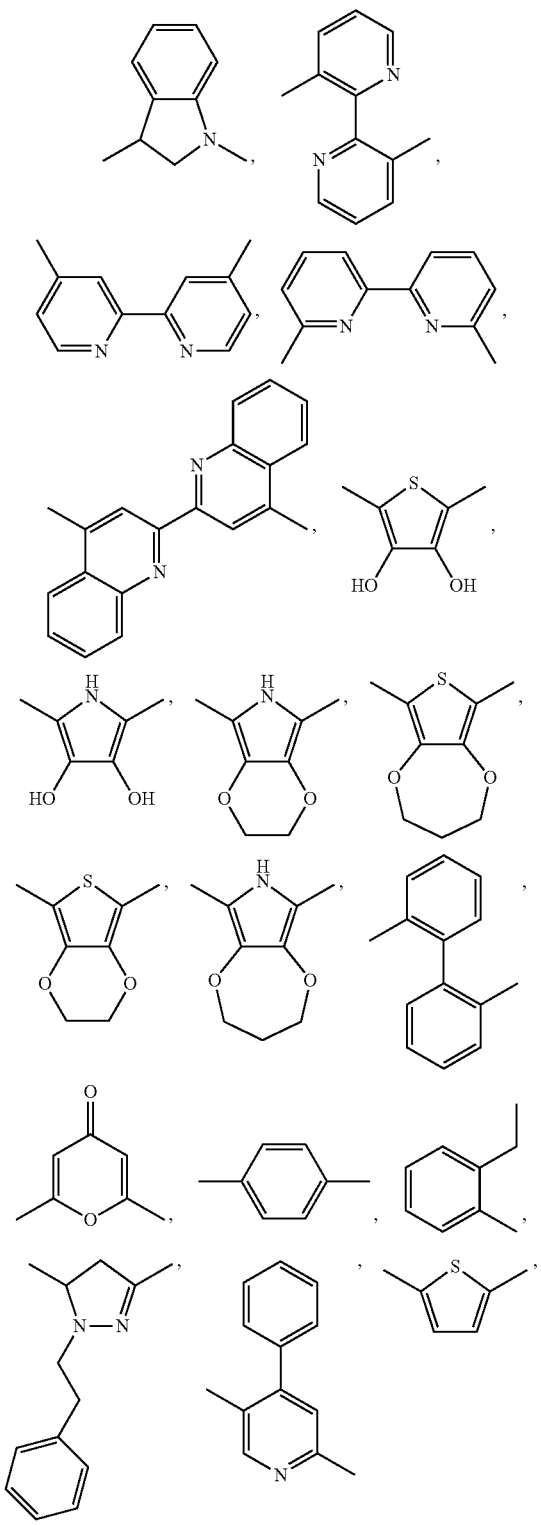

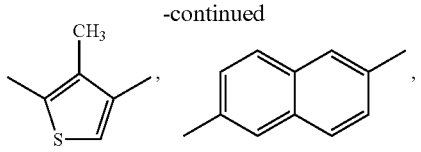

-continued

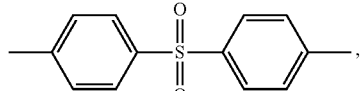

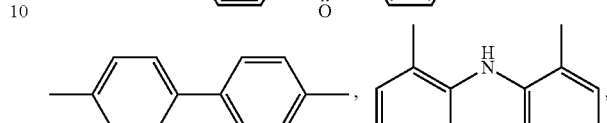

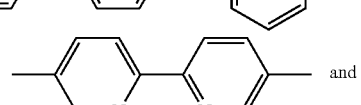

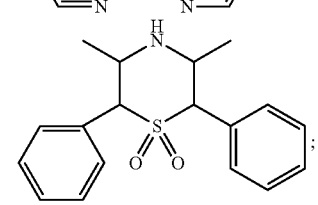

and
where $R^2$ =

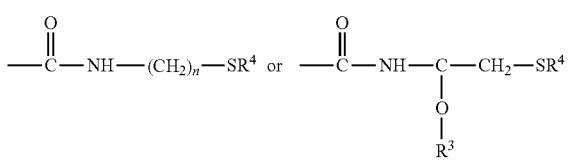

where $R^3$ = ethyl or methyl, $R^4$ = hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4. The $R^4$ attachment, other than hydrogen, converts the hydrophobic base compound to a hydrophilic, water soluble compound. The $R^3$ attachment makes the base compound susceptible to esterase conversion intracellular into a hydrophilic compound.

In accordance with yet another aspect of the present invention, a pharmaceutical composition is provided comprising:

a pharmaceutically effective amount of a compound having a chemical formula:

where $R^1$ =

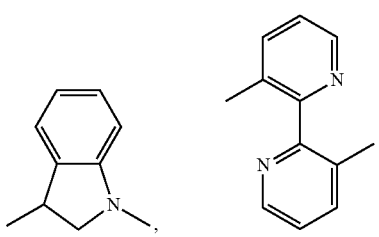

-continued

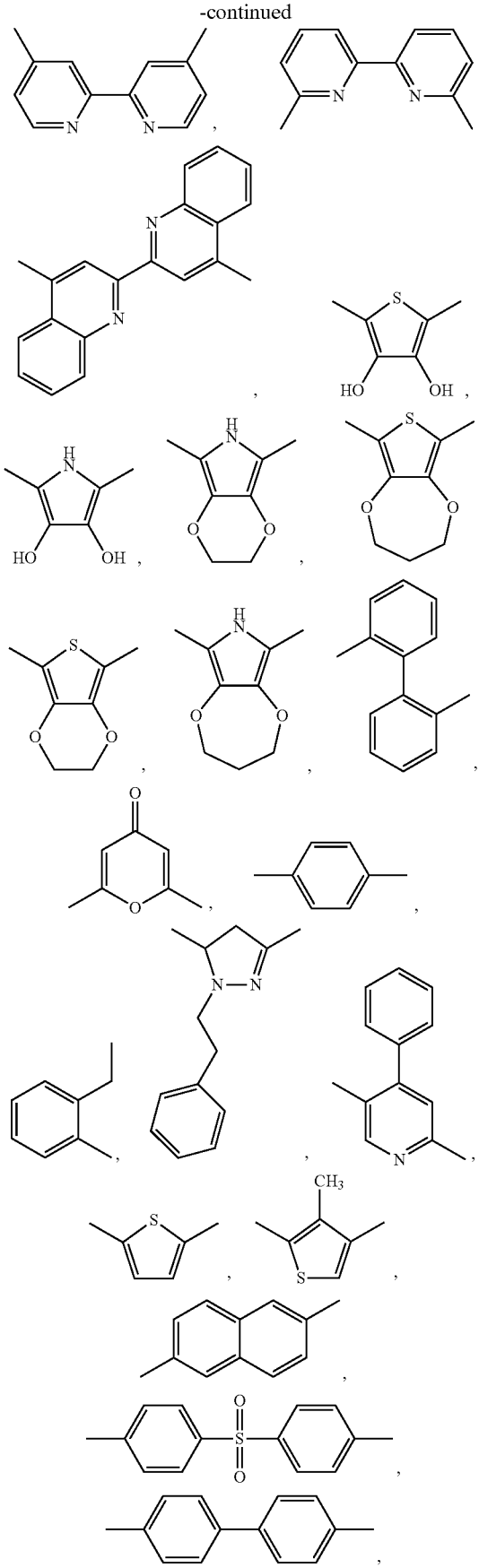

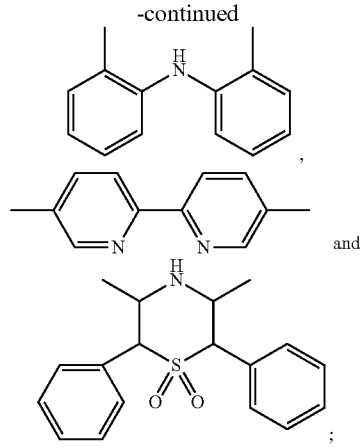

and and
where $R^2 =$

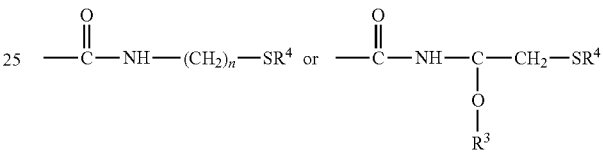

where $R^3 =$ ethyl or methyl, $R^4 =$ hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4; The $R^4$ attachment, other than hydrogen, converts the hydrophobic base compound to a hydrophilic, water soluble compound. The $R^3$ attachment makes the base compound susceptible to esterase conversion intracellular into a hydrophilic compound. and a pharmaceutically acceptable excipient.

In accordance with yet another aspect of the present invention, a pharmaceutical composition is provided comprising:

between about 99.5 and about 5 weight percent of a pharmaceutically effective amount of a compound having a chemical formula:

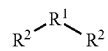

where $R^1 =$

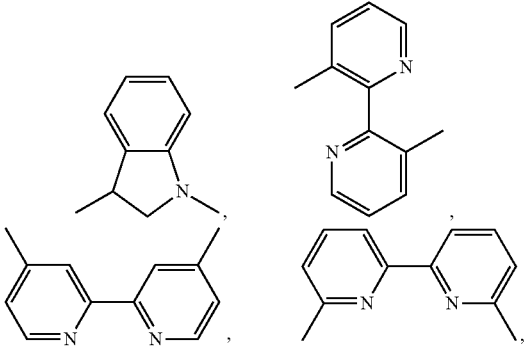

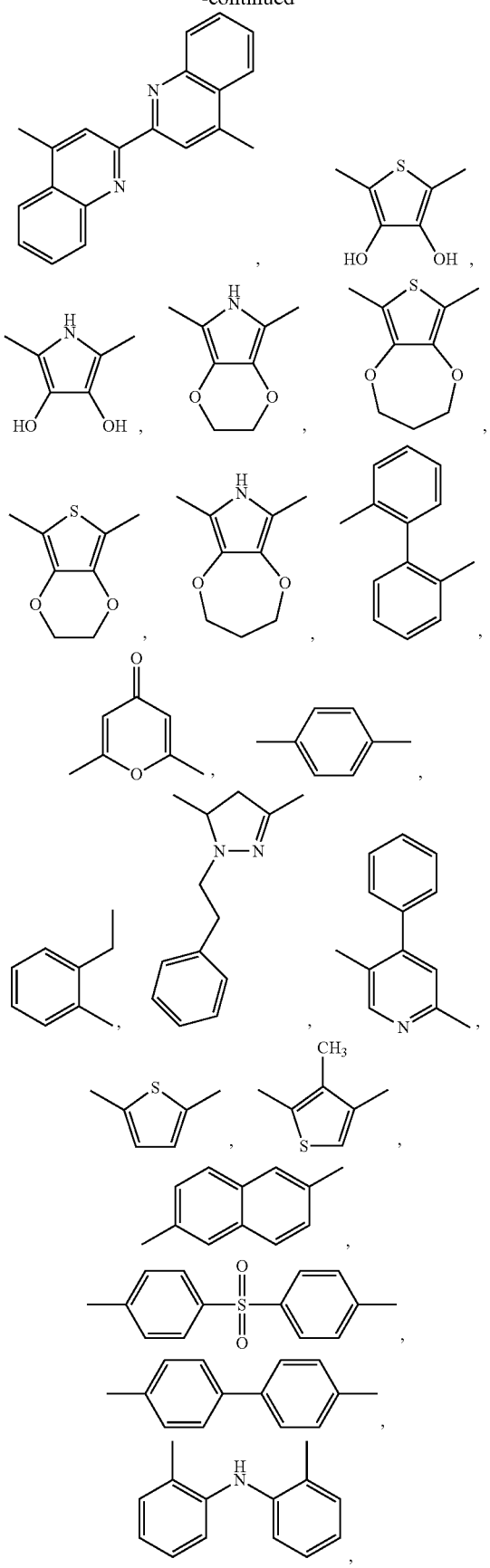

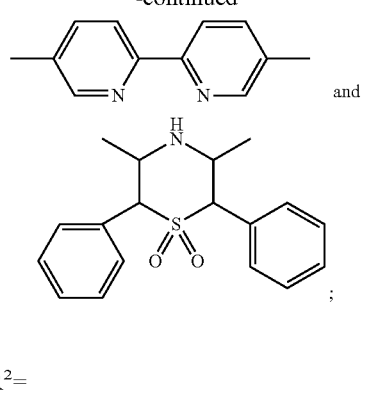

and

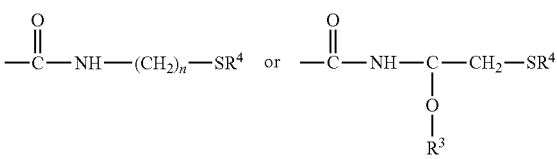

and
where $R^2=$ $$-\overset{O}{\underset{}{C}}-NH-(CH_2)_n-SR^4 \quad \text{or} \quad -\overset{O}{\underset{}{C}}-NH-\overset{}{\underset{\underset{R^3}{\overset{|}{O}}}{C}}-CH_2-SR^4$$

where $R^3$=ethyl or methyl, $R^4$=hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4; The $R^4$ attachment, other than hydrogen, converts the hydrophobic base compound to a hydrophilic, water soluble compound. The $R^3$ attachment makes the base compound susceptible to esterase conversion intracellular into a hydrophilic compound.

between about 0.0 and about 50 weight percent of an additional antioxidant;

between about 0.0 and about 20 weight percent of a water soluble metal chelator;

between about 0.0 and about 50 weight percent of glutathione;

between about 0.0 and about 50 weight percent of an additional dietary supplement that supports glutathione synthesis; and between about 0.5 and about 50 weight percent of a pharmaceutically acceptable excipient.

In the following description there is shown and described several different embodiments of the invention, simply by way of illustration of some of the modes best suited to carry out the invention. As it will be realized, the invention is capable of other different embodiments and its several details are capable of modification in various, obvious aspects all without departing from the invention.

DETAILED DESCRIPTION OF THE PREFERRED EMBODIMENTS OF THE INVENTION

The present invention relates to various methods of supplementing the diet of a mammal, removing heavy metals and other toxins from a mammal and relieving or ameliorating oxidative stress in a mammal. Each of the methods relies upon administering to said mammal a pharmaceutically effective amount of a compound having a chemical formula:

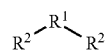

where R¹=

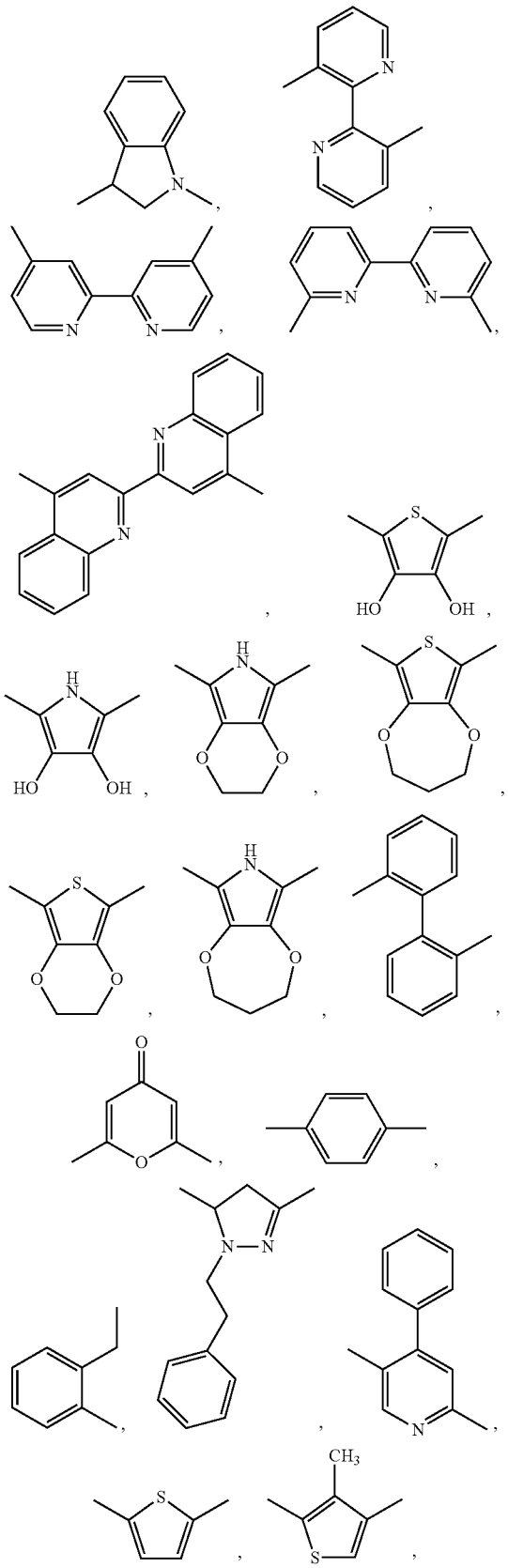

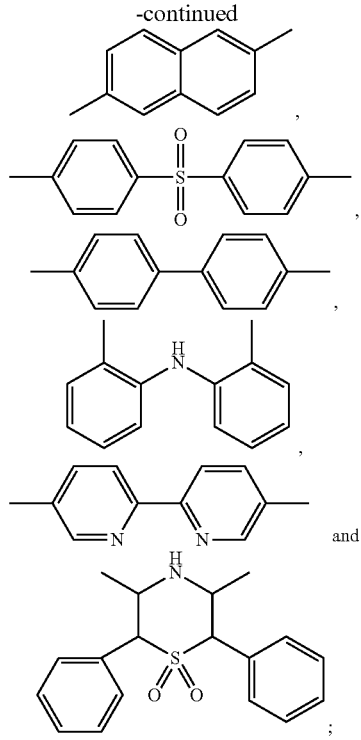

and
where R²=

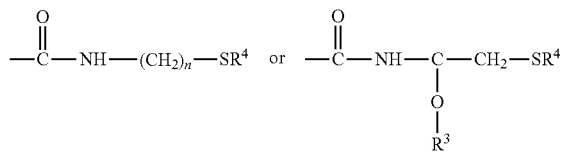

where R³=ethyl or methyl, R⁴=hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4. The R⁴ attachment, other than hydrogen, converts the hydrophobic base compound to a hydrophilic, water soluble compound. The R³ attachment makes the base compound susceptible to esterase conversion intracellular into a hydrophilic compound. The active compounds and their synthesis are described in detail in copending U.S. patent application Ser. No. 12/731,415 filed Mar. 25, 2010, the full disclosure of which is incorporated herein by reference.

The pharmaceutically effective amount of the compounds in question may be administered in any appropriate manner including, but not limited to, oral administration, transdermal administration, nasal administration, intravenous administration and administration by suppository. The method of supplementing a diet of a mammal includes administering between about 0.5 and about 40.0 mg of the compound per kilogram of the mammal's total body weight per day although, due to the lack of toxicity higher dose levels are acceptable. The compound may be administered in combination with another antioxidant or chelator. That antioxidant may be selected from a group including but not limited to vitamin-E, vitamin-D, cysteine, cystine, glutathione, lipoic acid and combinations thereof.

In the method of removing heavy metals and other toxins from a mammal, the compound is administered in an amount between about 0.5 and about 60.0 mg per kilogram of the mammal's total body weight per day. In this method the compound may be administered with a water soluble metal chelator. That water soluble metal chelator may be selected from a group consisting of glutathione (GSH), dihydrolipoic acid (DLPA), lipoic acid (LPA), N-acetylcysteine (NAC), dimercaptopropane sulfonate (DMPS), dimercaptosuccinic acid (DMSA), ethylenediaminetetraacetic acid (EDTA), and mixtures thereof. It should be appreciated, however, that other water soluble metal chelators besides those listed could be utilized.

In the method of relieving oxidative stress in a mammal the compound may be administered orally, transdermally, nasally, intravenously, injected subcutaneously, by suppository and other appropriate methods. Typically the compound is administered in an amount of between about 0.5 and about 100.0 mg of the compound per kilogram of the mammal's total body weight per day. The exceptionally low level of mammalian toxicity would also allow higher doses to be used in cases of acute toxicity or high oxidative stress. Here, it should also be noted that the present method may be used to treat oxidative stress resulting from virtually any cause or source including, but not limited to, heavy metal toxicity, drugs such as acetaminophen, xenobiotics, aging, infection, physical injury and disease.

These compounds are not used to directly produce intracellular glutathione and work primarily by salvaging naturally produced reduced glutathione (GSH) by the process of scavenging the intracellular ROSs preventing the oxidation to oxidized glutathione (GSSG). Also, the inhibitory binding of $Hg^{2+}$ and $Pb^{2+}$ and their removal from enzyme involved in the synthesis (e.g. glutatmine synthetase) and recovery of GSH (e.g. glutathione reductase) would additionally aid in the recovery of GSH to optimal levels. In accordance with an additional aspect of the present invention the compound may be administered with a precursor of glutathione. That glutathione precursor may be selected from a group of precursors consisting of cysteine, N-acetylcysteine, glycine, glutamate and combinations thereof. Also, removal of heavy metals from the iron-sulfur centers and other elements of the mitochondrial electron transport system would dramatically reduce the mitochondrial production of hydroxyl free radicals. It is well known that heavy metals make the mitochondria into hydroxyl free radical producing species where one heavy metal atom can cause the production of orders of magnitude higher levels of hydroxyl free radicals.

In yet another possible embodiment the compound is administered with a dietary supplement that supports glutathione synthesis. Such dietary supplements include, but are not limited to, whey protein, N-acetylcysteine, cysteine, glutathione, nicotine adenine dinucleotide ($NAD^+$), reduced nicotine adenine dinucleotide (NADH), glycylcysteine (glycyc), glutamylcysteine (glu-cys), and combinations thereof.

The compounds used in the present invention provide a number of unique benefits that make them attractive for use in methods of (a) supplementing the diet, (b) removing heavy metals and other toxins and (c) ameliorating oxidative stress in mammals. Many of the compounds exhibit very low if any toxicity and do not adversely affect commonly used blood/urine tests commonly used to measure human health. This low toxicity is attributed to the fact that the aromatic rings are attached to the sulfhydryl containing chains via an amide connection that contains a carboxylate attached to the aromatic system. Any cleavage of this bond would produce an aromatic carboxylate. Benzocarboxylate (e.g. monosodium benzoate, a food preservative) and many other benzoates, and other more complex carboxylated aromatic ring systems, are not usually toxic due to their hydrophilic nature and ease of excretion.

Advantageously the base compounds with hydrogen at $R^4$, are lipid soluble and, accordingly, after entering the plasma can enter cells of all tissues, cross the blood brain barrier and enter the bone marrow. This is important because the damage caused by heavy metals and the oxidative stress produced by hydroxyl free radicals and other free radicals of the reactive oxygen species mostly occur in the intracellular space. In contrast, most dietary antioxidants are water soluble and cannot enter into cells effectively nor can they cross the blood/brain barrier. As a further advantage, the lipid solubility of the compounds increases the time they spend in the body allowing them to be more effective at chelating heavy metals and scavenging hydroxyl free radicals. Chemical attachment of charged, natural compounds through the disulfide linkage produces water soluble analogs (for intravenous application) of the base compounds which would be rapidly reduced in the blood back to the original hydrophobic compounds and allow cell membrane permeation. Additionally, compounds containing the methylester and ethylester linkages offer the advantage of being made into charged water soluble species by enzymatic action of the natural esterases found in the mammalian body. This compound form starts out hydrophobic, can penetrate cell membranes after which it is convertible to the charged water soluble species by intracellular esterase activity, which may have advantages for excretion through the kidneys.

The compounds do not detectably disrupt any biochemical process in a mammal. They simply partition into the hydrophobic areas, bind heavy metals, react with free radicals eliminating them and are then excreted from the body primarily through the biliary transport system of the liver. The pharmaceutical compositions of the present invention are characterized by having relatively high ORAC (Oxygen-Radical-Absorbance-Capacity) scores. The ORAC score is measured by a compound or composition's ability to enter separate reactive oxygen species or free radicals and prevent them from oxidizing a water soluble fluorescent vitamin-E derivative. The pharmaceutical compositions of the present invention have the ability in the body to protect vitamin E (a fat soluble vitamin) and other fat soluble natural compounds such as lipids from damage by oxidizing free radicals since the compositions partition into the hydrophobic areas where they exist and react with free radicals more effectively thereby scavenging the hydroxyl free radicals and preventing them from doing damage. Significantly, vitamin-E has been recommended for Alzheimers diseased subjects to prevent oxidizing damage to their brain membranes or membrane lipids due to vitamin's E reactivity with hydroxyl free radicals. The pharmaceutical compositions of the present invention are more capable of reacting with these radicals than vitamin E and, accordingly, the pharmaceutical compositions should provide even better protection. Mass Spectrometry evaluations of some of the compounds after incubation with human and rat liver homogenates have shown that the major products produced were those with two and three oxygen atoms attached to the terminal sulfhydryl groups. This would convert the sulfhydryl (—SH) to higher oxidized levels such as sulfites ($-SO_3^-$) which are charged and eliminated through the kidneys.

The pharmaceutical compositions of the present invention are also characterized by an ability to increase the reduced (GSH) over oxidized (GSSG) glutathione ratio as well as to increase the total glutathione in the whole blood. Thus, more glutathione is available to scavenge free radicals and participate in the p-450 system to remove insoluble organic toxins from the membranes and cells. Thus, the body is better able to maintain a healthy glutathione level when the diet of the mammal is supplemented with compositions of the present invention.

Further, the pharmaceutical compositions of the present invention are characterized by good stability when stored. They also generally exhibit a very low odor level thereby making them more palatable for oral administration.

Generally, the pharmaceutical compositions of the present invention are better than glutathione delivered by IV or transdermally for increasing the intracellular level of glutathione. The rationale behind this is based on the very low level of glutathione found in the plasma versus the intercellular levels which are one thousand to ten thousand times higher. Any glutathione molecule that enters the blood by IV or transdermal delivery is immediately bound and removed by the glutathione receptors in the liver that are used to take glutathione labeled toxins and viruses out of the plasma and place them in the bile (biliary transport system). Glutathione in the blood would not remain long enough to enter cells where it could be used, plus do to its highly charged character (2 negative and 1 positive charges/molecule) GSH would have to enter via specific carriers in the face of a significant concentration gradient that would prevent this. This statement is based on the fact that many water insoluble toxicants are removed from the body by first oxidizing them, attaching glutathione (by the enzyme glutathione-s-transferase) to this oxidized site on the toxin, then actively transporting the glutathione labeled toxicant out of the cell and into the blood where it is actively removed by the glutathione receptors of the biliary transport system. In contrast, pharmaceutical compositions of the present invention face no concentration gradients and can enter all cells and due to their hydrophobic nature, insert to some degree into the lipid membrane or other hydrophobic sites where they can scavenge hydroxyl free radicals, the major chemical species that oxidize glutathione and cause its levels to drop. The pharmaceutical compositions salvage naturally produced glutathione intracellular enhancing its longevity and raising glutathione levels in-vivo without having to battle transport across a membrane against a high gradient of glutathione.

Pharmaceutical compositions of the present invention may be prepared by combining a pharmaceutically effective amount of a compound having a chemical formula:

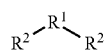

where $R^1$=

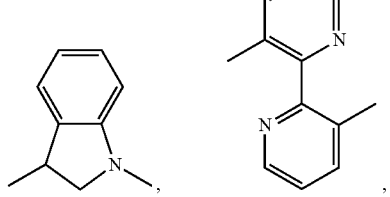

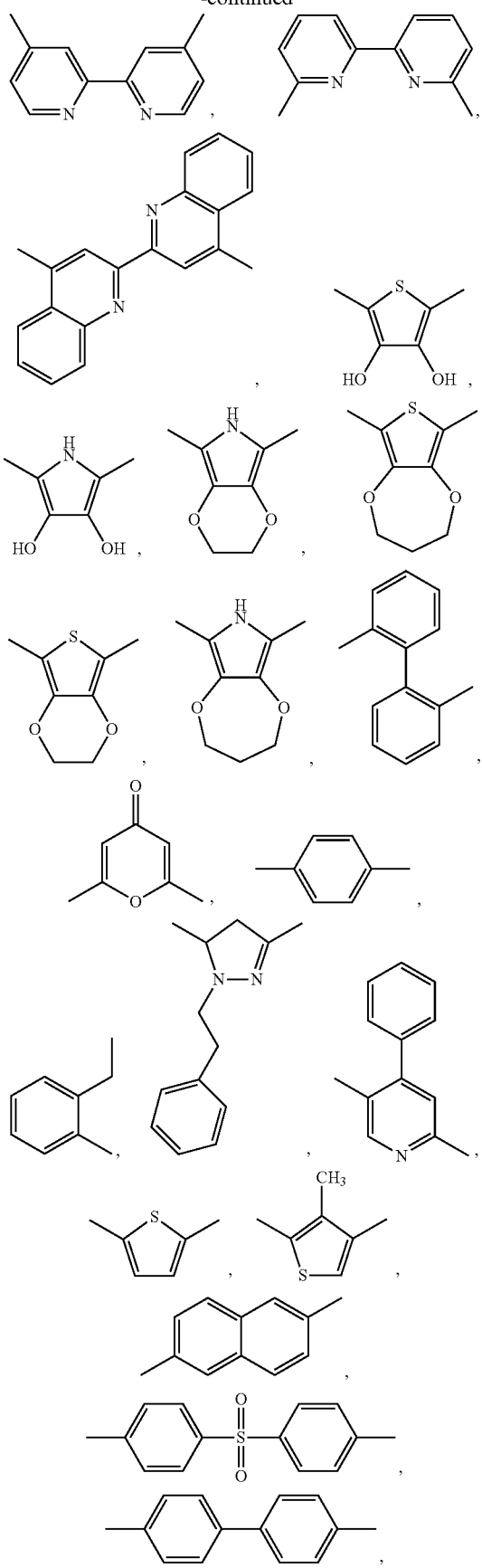

-continued

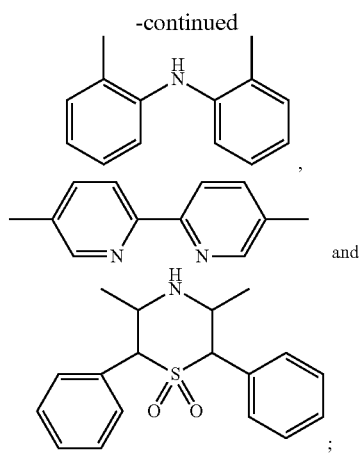

and
where $R^2$=

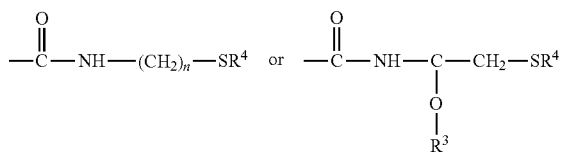

where $R^3$=ethyl or methyl, $R^4$=hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n 2-4, with an excipient. Substantially any suitable excipient may be utilized including but not limited to albumin, almond oil, ascorbic acid, benzoic acid, calcium stearate, canola oil, calcium carboxymethylcellulose, sodium carboxymethylcellulose, castor oil, hydrogenated castor oil, microcrystalline cellulose, corn oil, cotton seed oil, cyclodextrins, ethylene glycol palmitostearate, gelatin, glycerin, hydroxyethyl cellulose, hydroxyethylmethyl cellulose, hydroxypropyl cellulose, hypermellose, low-substituted hydroxypropyl cellulose, lanolin, linoleic acid, magnesium silicate, magnesium stearate, medium-chain triglycerides, mineral oil, olive oil, peanut oil, pectin, compressible sugar, sunflower oil, hydrogenated vegetable oil, water and combinations thereof. In order to provide multiple antioxidant potential, the pharmaceutical compositions may further include other antioxidants including, but not limited to vitamin-E, vitamin-D, cystine, glutathione, lipoic acid and combinations thereof. Further the pharmaceutical compositions may include a water soluble metal chelator to enhance removal of toxic metals both through the liver and kidney and with an enhanced rate. Substantially, any suitable water soluble metal chelator may be utilized including but not limited to glutathione (GSH), dihydrolipoic acid (DLPA), lipoic acid (LPA), N-acetylcysteine (NAC), dimercaptopropane sulfonate (DMPS), dimercaptosuccinic acid (DMSA), ethylenediaminetetraacetic acid (EDTA), and mixtures thereof. Further, in order to further enhance the levels of glutathione in the subject, the pharmaceutical compositions may include a precursor of glutathione which may be selected from a group including but not limited to cysteine, glycine, glutamate and combinations thereof. Further pharmaceutical compositions may include a dietary supplement that supports glutathione synthesis. Substantially any appropriate dietary supplement that supports glutathione synthesis may be utilized including but not limited to whey protein, N-acetylcystein, cysteine, glutathione, nicotine adenine dinucleotide (NAD$^+$), reduced nicotine adenine dinucleotide (NADH), glycylcysteine (gly-cys), glutamylcysteine (glu-cyc), and combinations thereof. Pharmaceutical compositions may also include various binders, preservatives, mineral supplements, bulking agents, diluents, carriers, flavoring agents that are widely known to be used in pharmaceutical compositions. Exemplary pharmaceutical compositions include between about 95.5 and about 85 weight percent active compound, between about 0.5 and about 15 weight percent excipient. The optional additional antioxidant(s) may be provided at between about 0 and about 50 weight percent. The optional additional water soluble metal chelator may be provided at between about 0 and about 20 weight percent. The optional additional precursor of glutathione may be provided at between about 0 and about 50 weight percent. Further the optionally additional dietary supplement that supports glutathione synthesis may be provided at between about 0 and about 50 weight percent. One or more of any of the optional additives may be included. The optional additive replaces a like percentage of the compound in the final composition.

Preferred dosage forms for oral administration include the isolated compounds in powder form. Such powders may be taken up with a scoup and spread onto food or mixed into drinks for easy consumption without bad taste. The pure compounds may be pre-mixed with certain dietary ingredients such as butter, olive oil, corn oil, albumin, whey or other foods which will help in absorption of the compounds by the mere process of dissolving them. It has been determined that it takes about two hours post ingestion for the maximum level of active ingredient to show up in the plasma of all tested animals. Further, after 24 hours post-ingestion the active ingredient levels were shown to drop between 4-12% of the peak values seen at hour 2.

Some of the commercially available solubilizers that can be used for parenteral (injectible), oral, topical or intranasal delivery in different combinations and ratios according to need include: (a) co-solvents such as polyethylene glycol 300/400, Macrogol 300/400, Lutrol E300/E400, propylene glycol, Soluphor P and NMP; (b) PEG derivatives such as Cremophor RH40, Cremophor EL/ELP and Solutol HS-15; and (c) polyoxamers such as Lutrol F68, Lutrol F127, Lutrol Micro 68 and Lutrol Micro 127.

The pure compound may be encapsulated in several weight forms (eg. 50, 100, 200, 500 mg/capsule) and taken orally. The pure compound may be mixed with excipients (eg. microcrystalline cellulose, hypermellose, magnesium stearate) to provide a mixed material that can be efficiently encapsulated by machines for mass production at a rapid rate.

The pure compound may also be made into tablet form by mixing with common agents or binders used to induce adhesive properties for tablet formation.

Any of the other hydrophobic compounds may be dissolved in simple oils and applied to the skin. The compounds dissolved in DMSO (dimethylsulfoxide) are rapidly taken up through the skin without local irritation. Also, dissolving the compounds in warm butter allows them to be applied transdermally.

The compounds may be placed in suppository capsules either in powder form or dissolved in oils or as mixed with protein based material (eg. human serum albumin, HSA) for delivery. The compounds may also be dissolved in human serum albumin for intravenous delivery. Similarly, blood could be pulled from a patient and the compounds added to that blood before being returned to the patient. This property is allowed as HSA is a water soluble protein with hydrophobic areas designed to carry natural hydrophobic molecules through the blood to cells where they are transferred to cell membranes.

The compositions and methods of the present invention may be accomplished by various means which are illustrated in the examples below. These examples are intended to be illustrative only as numerous modifications and variations will be apparent to those skilled in the art.

EXAMPLE 1

Compounds have been produced and used by test animals and humans in pure powder form in resealable plastic bags accompanied with a pharmaceutical spoon that allows delivery of compound at 50 to 100 mg/spoonful. The pure powder can be taken directly into the oral cavity for sublingual delivery or mixed with foods and drinks. The mixing of these compounds has been done with oily foods such as butter, olive oil, peanut butter to enhance their solubilization prior to ingestion and uptake in the digestive tract.

EXAMPLE 2

Compounds have been mixed with excipients magnesium stearate, microcrystalline cellulose, hypermellose and silicon dioxide to form a pharmaceutical composition administered in capsules of 50, 100 and 200 mg quantities of compound for oral ingestion by humans.

EXAMPLE 3

Compounds have been dissolved in natural oils such as olive oil, cod liver oil, corn oil, butter and taken orally by humans.

EXAMPLE 4

Compounds have been dissolved in natural oils such as olive oil, cod liver oil, corn oil, butter and applied to the skin with rubbing to affect a transdermal delivery of the compound into humans.

EXAMPLE 5

Compounds have been dissolved in DMSO (dimethylsulfoxide):isotonic sodium chloride (25%:75% mixtures) and injected subcutaneously into test animals with excellent results.

EXAMPLE 6

Compounds have been dissolved in Solutol HS 15 and NMP mixtures for both subcutaneous and intravenous delivery into test animals as follows:
 1. Prepare 1:1 w/v of NMP and Solutol HS 15
 2. Weigh out the required amount of the pharmaceutically effective compound in powder form.
 3. Add required amount of the 1:1 mixture. (20% of final volume)
 4. Vortex to make sure that the compound is in solution.
 5. Slowly add the Normal saline (80% of final volume)
 6. Sonicate for a few minutes to get a clear solution.

EXAMPLE 7

Pharmaceutically effective compounds of the invention have been dissolved in Cremophor and ethyl alcohol mixtures for both subcutaneous and intravenous delivery into test animals as follows:

1. Prepare a 1:1 w/v of ethyl alcohol and Cremophor.
 2. Weigh out the required amount of OSR#1 powder.
 3. Add the required amount to the 1:1 mixture.
 4. Vortex to make sure OSR is in solution.
 5. Sonicate if necessary for a few minutes.
 6. Slowly add Normal Saline 50 to 80% of the final volume.

EXAMPLE 8

A dosing solution for intravenous administration (IV) into test animals was prepared at 1 mg/mL in a formulation consisting of 80% normal saline (NS) and 20% of a 1:1 mixture of N-methylpyrrolidone (NMP) and Solutol HS15. This was used successfully to determine the plasma half life of one of the compounds in mice.

EXAMPLE 9

Medicament and/or preparation of dosage form. To prepare a medicament and/or suitable dosage form, the pharmaceutically active compound of the invention may be admixed and/or contacted with one or more of the excipients listed in Table 9-1.

TABLE 9-1

| Excipients |
| --- |
| Acacia |
| Acesulfame Potassium |
| Acetic Acid, Glacial |
| Acetone |
| Acetyltributyl Citrate |
| Acetyltriethyl Citrate |
| Agar |
| Albumin |
| Alcohol |
| Alginic Acid |
| Aliphatic Polyesters |
| Alitame |
| Almond Oil |
| Alpha Tocopherol |
| Aluminum Hydroxide Adjuvant |
| Aluminum Oxide |
| Aluminum Phosphate Adjuvant |
| Aluminum Stearate |
| Ammonia Solution |
| Ammonium Alginate |
| Ascorbic Acid |
| Ascorbyl Palmitate |
| Aspartame |
| Attapulgite |
| Bentonite |
| Benzalkonium Chloride |
| Benzethonium Chloride |
| Benzoic Acid |
| Benzyl Alcohol |
| Benzyl Benzoate |
| Boric Acid |
| Bronopol |
| Butylated Hydroxyanisole |
| Butylated Hydroxytoluene |
| Butylparaben |
| Calcium Alginate |
| Calcium Carbonate |
| Calcium Phosphate, Dibasic Anhydrous |
| Calcium Phosphate, Dibasic Dihydrate |
| Calcium Phosphate, Tribasic |
| Calcium Stearate |
| Calcium Sulfate |
| Canola Oil |
| Carbomer |
| Carbon Dioxide |
| Carboxymethylcellulose Calcium |
| Carboxymethylcellulose Sodium |
| Carrageenan |

TABLE 9-1-continued

| Excipients |
|---|
| Castor Oil |
| Castor Oil, Hydrogenated |
| Cellulose, Microcrystalline |
| Cellulose, Powdered |
| Cellulose, Silicified Microcrystalline |
| Cellulose Acetate |
| Cellulose Acetate Phthalate |
| Ceratonia |
| Cetostearyl Alcohol |
| Cetrimide |
| Cetyl Alcohol |
| Cetylpyridinium Chloride |
| Chitosan |
| Chlorhexidine |
| Chlorobutanol |
| Chlorocresol |
| Chlorodifluoroethane (HCFC) |
| Chlorofluorocarbons (CFC) |
| Chloroxylenol |
| Cholesterol |
| Citric Acid Monohydrate |
| Colloidal Silicon Dioxide |
| Coloring Agents |
| Copovidone |
| Corn Oil |
| Cottonseed Oil |
| Cresol |
| Croscarmellose Sodium |
| Crospovidone |
| Cyclodextrins |
| Cyclomethicone |
| Denatonium Benzoate |
| Dextrates |
| Dextrin |
| Dextrose |
| Dibutyl Phthalate |
| Dibutyl Sebacate |
| Diethanolamine |
| Diethyl Phthalate |
| Difluoroethane (HFC) |
| Dimethicone |
| Dimethyl Ether |
| Dimethyl Phthalate |
| Dimethyl Sulfoxide |
| Dimethylacetamide |
| Disodium Edetate |
| Docusate Sodium |
| Edetic Acid |
| Erythorbic Acid |
| Erythritol |
| Ethyl Acetate |
| Ethyl Lactate |
| Ethyl Maltol |
| Ethyl Oleate |
| Ethyl Vanillin |
| Ethylcellulose |
| Ethylene Glycol Palmitostearate |
| Ethylene Vinyl Acetate |
| Ethylparaben |
| Fructose |
| Fumaric Acid |
| Gelatin |
| Glucose, Liquid |
| Glycerin |
| Glyceryl Behenate |
| Glyceryl Monooleate |
| Glyceryl Monostearate |
| Glyceryl Palmitostearate |
| Glycofurol |
| Guar Gum |
| Hectorite |
| Heptafluoropropane (HFC) |
| Hexetidine |
| Hydrocarbons (HC) |
| Hydrochloric Acid |
| Hydroxyethyl Cellulose |
| Hydroxyethylmethyl Cellulose |
| Hydroxypropyl Cellulose |

TABLE 9-1-continued

| Excipients |
|---|
| Hydroxypropyl Cellulose, Low-substituted |
| Hydroxypropyl Starch |
| Hypromellose |
| Hypromellose Acetate Succinate |
| Hypromellose Phthalate |
| Imidurea |
| Inulin |
| Iron Oxides |
| Isomalt |
| Isopropyl Alcohol |
| Isopropyl Myristate |
| Isopropyl Palmitate |
| Kaolin |
| Lactic Acid |
| Lactitol |
| Lactose, Anhydrous |
| Lactose, Monohydrate |
| Lactose, Spray-Dried |
| Lanolin |
| Lanolin, Hydrous |
| Lanolin Alcohols |
| Lauric Acid |
| Lecithin |
| Leucine |
| Linoleic Acid |
| Macrogol 15 Hydroxystearate |
| Magnesium Aluminum Silicate |
| Magnesium Carbonate |
| Magnesium Oxide |
| Magnesium Silicate |
| Magnesium Stearate |
| Magnesium Trisilicate |
| Malic Acid |
| Maltitol |
| Maltitol Solution |
| Maltodextrin |
| Maltol |
| Maltose |
| Mannitol |
| Medium-chain Triglycerides |
| Meglumine |
| Menthol |
| Methylcellulose |
| Methylparaben |
| Mineral Oil |
| Mineral Oil, Light |
| Mineral Oil and Lanolin Alcohols |
| Monoethanolamine |
| Monosodium Glutamate |
| Monothioglycerol |
| Myristic Acid |
| Neohesperidin Dihydrochalcone |
| Nitrogen |
| Nitrous Oxide |
| Octyldodecanol |
| Oleic Acid |
| Oleyl Alcohol |
| Olive Oil |
| Palmitic Acid |
| Paraffin |
| Peanut Oil |
| Pectin |
| Petrolatum and Lanolin Alcohols |
| Petrolatum |
| Phenol |
| Phenoxyethanol |
| Phenylethyl Alcohol |
| Phenylmercuric Acetate |
| Phenylmercuric Borate |
| Phenylmercuric Nitrate |
| Phosphoric Acid |
| Polacrilin Potassium |
| Poloxamer |
| Polycarbophil |
| Polydextrose |
| Polyethylene Glycol |
| Polyethylene Oxide |
| Polymethacrylates |

TABLE 9-1-continued

| Excipients |
| --- |
| Poly(methyl vinyl ether/maleic anhydride) |
| Polyoxyethylene Alkyl Ethers |
| Polyoxyethylene Castor Oil Derivatives |
| Polyoxyethylene Sorbitan Fatty Acid Esters |
| Polyoxyethylene Stearates |
| Polyvinyl Acetate Phthalate |
| Polyvinyl Alcohol |
| Potassium Alginate |
| Potassium Benzoate |
| Potassium Bicarbonate |
| Potassium Chloride |
| Potassium Citrate |
| Potassium Hydroxide |
| Potassium Metabisulfite |
| Potassium Sorbate |
| Povidone |
| Propionic Acid |
| Propyl Gallate |
| Propylene Carbonate |
| Propylene Glycol |
| Propylene Glycol Alginate |
| Propylparaben |
| 2-Pyrrolidone |
| Raffinose |
| Saccharin |
| Saccharin Sodium |
| Saponite |
| Sesame Oil |
| Shellac |
| Simethicone |
| Sodium Acetate |
| Sodium Alginate |
| Sodium Ascorbate |
| Sodium Benzoate |
| Sodium Bicarbonate |
| Sodium Borate |
| Sodium Chloride |
| Sodium Citrate Dihydrate |
| Sodium Cyclamate |
| Sodium Hyaluronate |
| Sodium Hydroxide |
| Sodium Lactate |
| Sodium Lauryl Sulfate |
| Sodium Metabisulfite |
| Sodium Phosphate, Dibasic |
| Sodium Phosphate, Monobasic |
| Sodium Propionate |
| Sodium Starch Glycolate |
| Sodium Stearyl Fumarate |
| Sodium Sulfite |
| Sorbic Acid |
| Sorbitan Esters (Sorbitan Fatty Acid Esters) |
| Sorbitol |
| Soybean Oil |
| Starch |
| Starch, Pregelatinized |
| Starch, Sterilizable Maize |
| Stearic Acid |
| Stearyl Alcohol |
| Sucralose |
| Sucrose |
| Sugar, Compressible |
| Sugar, Confectioner's |
| Sugar Spheres |
| Sulfobutylether β-Cyclodextrin |
| Sulfuric Acid |
| Sunflower Oil |
| Suppository Bases, Hard Fat |
| Talc |
| Tartaric Acid |
| Tetrafluoroethane (HFC) |
| Thaumatin |
| Thymol |
| Titanium Dioxide |
| Tragacanth |
| Trehalose |
| Triacetin |
| Tributyl Citrate |

TABLE 9-1-continued

| Excipients |
| --- |
| Triethanolamine |
| Triethyl Citrate |
| Vanillin |
| Vegetable Oil, Hydrogenated |
| Water |
| Wax, Anionic Emulsifying |
| Wax, Carnauba |
| Wax, Cetyl Esters |
| Wax, Microcrystalline |
| Wax, Nonionic Emulsifying |
| Wax, White |
| Wax, Yellow |
| Xanthan Gum |
| Xylitol |
| Zein |
| Zinc Acetate |
| Zinc Stearate |

EXAMPLE 10

Dosage form. A suitable dosage form for administration of the pharmaceutically active compound of the present invention may be chosen from among the dosage forms listed in Table 10-1.

TABLE 10-1

Dosage forms

| NAME | DEFINITION |
| --- | --- |
| AEROSOL | A product that is packaged under pressure and contains therapeutically active ingredients that are released upon activation of an appropriate valve system; it is intended for topical application to the skin as well as local application into the nose (nasal aerosols), mouth (lingual aerosols), or lungs (inhalation aerosols). |
| AEROSOL, POWDER | A product that is packaged under pressure and contains therapeutically active ingredients, in the form of a powder, that are released upon activation of an appropriate valve system. |
| BAR, CHEWABLE | A solid dosage form usually in the form of a rectangle that is meant to be chewed. |
| CAPSULE | A solid oral dosage form consisting of a shell and a filling. The shell is composed of a single sealed enclosure, or two halves that fit together and which are sometimes sealed with a band. Capsule shells may be made from gelatin, starch, or cellulose, or other suitable materials, may be soft or hard, and are filled with solid or liquid ingredients that can be poured or squeezed. |
| CAPSULE, COATED | A solid dosage form in which the drug is enclosed within either a hard or soft soluble container or "shell" made from a suitable form of gelatin; additionally, the capsule is covered in a designated coating. |
| CAPSULE, COATED PELLETS | A solid dosage form in which the drug is enclosed within either a hard or soft soluble container or "shell" made from a suitable form of gelatin; the drug itself is in the form of granules to which varying amounts of coating have been applied. |
| CAPSULE, COATED, EXTENDED RELEASE | A solid dosage form in which the drug is enclosed within either a hard or soft soluble container or "shell" made from a suitable form of gelatin; additionally, the capsule is covered in a designated coating, and which releases a drug (or drugs) in such a manner to allow at least a reduction in dosing frequency as compared to that drug (or drugs) presented as a conventional dosage form. |

TABLE 10-1-continued

Dosage forms

| NAME | DEFINITION |
|---|---|
| CAPSULE, DELAYED RELEASE | A solid dosage form in which the drug is enclosed within either a hard or soft soluble container made from a suitable form of gelatin, and which releases a drug (or drugs) at a time other than promptly after administration. Enteric-coated articles are delayed release dosage forms. |
| CAPSULE, DELAYED RELEASE PELLETS | A solid dosage form in which the drug is enclosed within either a hard or soft soluble container or "shell" made from a suitable form of gelatin; the drug itself is in the form of granules to which enteric coating has been applied, thus delaying release of the drug until its passage into the intestines. |
| CAPSULE, EXTENDED RELEASE | A solid dosage form in which the drug is enclosed within either a hard or soft soluble container made from a suitable form of gelatin, and which releases a drug (or drugs) in such a manner to allow a reduction in dosing frequency as compared to that drug (or drugs) presented as a conventional dosage form. |
| CAPSULE, FILM COATED, EXTENDED RELEASE | A solid dosage form in which the drug is enclosed within either a hard or soft soluble container or "shell" made from a suitable form of gelatin; additionally, the capsule is covered in a designated film coating, and which releases a drug (or drugs) in such a manner to allow at least a reduction in dosing frequency as compared to that drug (or drugs) presented as a conventional dosage form. |
| CAPSULE, GELATIN COATED | A solid dosage form in which the drug is enclosed within either a hard or soft soluble container made from a suitable form of gelatin; through a banding process, the capsule is coated with additional layers of gelatin so as to form a complete seal. |
| CAPSULE, LIQUID FILLED | A solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle. |
| CONCENTRATE | A liquid preparation of increased strength and reduced volume which is usually diluted prior to administration. |
| CORE, EXTENDED RELEASE | An ocular system placed in the eye from which the drug diffuses through a membrane at a constant rate over a specified period. |
| CREAM | An emulsion, semisolid[3] dosage form, usually containing >20% water and volatiles5 and/or <50% hydrocarbons, waxes, or polyols as the vehicle. This dosage form is generally for external application to the skin or mucous membranes. |
| CREAM, AUGMENTED | A cream dosage form that enhances drug delivery. Augmentation does not refer to the strength of the drug in the dosage form. NOTE: CDER has decided to refrain from expanding the use of this dosage form due to difficulties in setting specific criteria that must be met to be considered "augmented". |
| DRUG DELIVERY SYSTEM | Modern technology, distributed with or as a part of a drug product that allows for the uniform release or targeting of drugs to the body. |
| ELIXIR | A clear, pleasantly flavored, sweetened hydroalcoholic liquid containing dissolved medicinal agents; it is intended for oral use. |
| EMULSION | A dosage form consisting of a two-phase system comprised of at least two immiscible liquids[1], one of which is dispersed as droplets (internal or dispersed phase) within the other liquid (external or continuous phase), generally stabilized with one or more emulsifying agents. (Note: Emulsion is used as a dosage form term unless a more specific term is applicable, e.g. cream, lotion, ointment.) |
| ENEMA | A rectal preparation for therapeutic, diagnostic, or nutritive purposes. |
| EXTRACT | A concentrated preparation of vegetable or animal drugs obtained by removal of the active constituents of the respective drugs with a suitable menstrua, evaporation of all or nearly all of the solvent, and adjustment of the residual masses or powders to the prescribed standards. |
| FIBER, EXTENDED RELEASE | A slender and elongated solid thread-like substance that delivers drug in such a manner to allow a reduction in dosing frequency as compared to that drug (or drugs) presented as a conventional dosage form. |
| FILM, SOLUBLE | A thin layer or coating which is susceptible to being dissolved when in contact with a liquid. |
| FOR SOLUTION | A product, usually a solid, intended for solution prior to administration. |
| FOR SUSPENSION | A product, usually a solid, intended for suspension prior to administration. |
| FOR SUSPENSION, EXTENDED RELEASE | A product, usually a solid, intended for suspension prior to administration; once the suspension is administered, the drug will be released at a constant rate over a specified period. |
| GEL | A semisolid[3] dosage form that contains a gelling agent to provide stiffness to a solution or a colloidal dispersion.[4] A gel may contain suspended particles. |
| GLOBULE | Also called pellets or pilules, are made of pure sucrose, lactose, or other polysaccharides. They are formed into small globular masses of various sizes, and are medicated by placing them in a vial and adding the liquid drug attenuation in the proportion not less than one percent (v/w). After shaking, the medicated globules are dried at temperatures not to exceed 40 degrees Centigrade. |
| GRANULE | A small particle or grain. |
| GRANULE, DELAYED RELEASE | A small medicinal particle or grain to which an enteric or other coating has been applied, thus delaying release of the drug until its passage into the intestines. |
| GRANULE, EFFERVESCENT | A small particle or grain containing a medicinal agent in a dry mixture usually composed of sodium bicarbonate, citric acid, and tartaric acid which, when in contact with water, has the capability to release gas, resulting in effervescence. |
| GRANULE, FOR SOLUTION | A small medicinal particle or grain made available in its more stable dry form, to be reconstituted with solvent just before dispensing; the granules are so prepared to contain not only the medicinal agent, but the colorants, flavorants, and any other desired pharmaceutic ingredient. |
| GRANULE, FOR SUSPENSION | A small medicinal particle or grain made available in its more stable dry form, to be reconstituted with solvent just before dispensing to form a suspension; the granules are so prepared to contain not only the medicinal agent, but the colorants, flavorants, and any other desired pharmaceutic ingredient. |
| GRANULE, FOR SUSPENSION, EXTENDED RELEASE | A small medicinal particle or grain made available in its more stable dry form, to be reconstituted with solvent just before dispensing to form a suspension; the extended release system achieves slow release of the drug over an extended period of time and maintains constant drug levels in the blood or target tissue. |
| INJECTABLE, LIPOSOMAL | An injection, which either consists of or forms liposomes (a lipid bilayer vesicle usually composed of phospholipids which is used to encapsulate an active drug substance). |
| INJECTION | A sterile preparation intended for parenteral use; five distinct classes of injections exist as defined by the USP. |
| INJECTION, EMULSION | An emulsion consisting of a sterile, pyrogen-free preparation intended to be administered parenterally. |
| INJECTION, LIPID COMPLEX | [definition pending] |

TABLE 10-1-continued

Dosage forms

| NAME | DEFINITION |
|---|---|
| INJECTION, POWDER, FOR SOLUTION | A sterile preparation intended for reconstitution to form a solution for parenteral use. |
| INJECTION, POWDER, FOR SUSPENSION | A sterile preparation intended for reconstitution to form a suspension for parenteral use. |
| INJECTION, POWDER, FOR SUSPENSION, EXTENDED RELEASE | A dried preparation intended for reconstitution to form a suspension for parenteral use which has been formulated in a manner to allow at least a reduction in dosing frequency as compared to that drug presented as a conventional dosage form (e.g., as a solution). |
| INJECTION, POWDER, LYOPHILIZED, FOR LIPOSOMAL SUSPENSION | A sterile freeze dried preparation intended for reconstitution for parenteral use which has been formulated in a manner that would allow liposomes (a lipid bilayer vesicle usually composed of phospholipids which is used to encapsulate an active drug substance, either within a lipid bilayer or in an aqueous space) to be formed upon reconstitution. |
| INJECTION, SUSPENSION, LIPOSOMAL | A liquid preparation, suitable for injection, which consists of an oil phase dispersed throughout an aqueous phase in such a manner that liposomes (a lipid bilayer vesicle usually composed of phospholipids which is used to encapsulate an active drug substance, either within a lipid bilayer or in an aqueous space) are formed. |
| INJECTION, SUSPENSION, SONICATED | A liquid preparation, suitable for injection, which consists of solid particles dispersed throughout a liquid phase in which the particles are not soluble. In addition, the product is sonicated while a gas is bubbled through the suspension, and this results in the formation of microspheres by the solid particles. |
| JELLY | A class of gels, which are semisolid systems that consist of suspensions made up of either small inorganic particles or large organic molecules interpenetrated by a liquid—in which the structural coherent matrix contains a high portion of liquid, usually water. |
| KIT | A packaged collection of related material. |
| LINIMENT | A solution or mixture of various substances in oil, alcoholic solutions of soap, or emulsions intended for external application. |
| LIQUID, EXTENDED RELEASE | A liquid that delivers a drug in such a manner to allow a reduction in dosing frequency as compared to that drug (or drugs) presented as a conventional dosage form. |
| LOTION | An emulsion, liquid[1] dosage form. This dosage form is generally for external application to the skin.[2] |
| LOTION, AUGMENTED | A lotion dosage form that enhances drug delivery. Augmentation does not refer to the strength of the drug in the dosage form. NOTE: CDER has decided to refrain from expanding the use of this dosage form due to difficulties in setting specific criteria that must be met to be considered "augmented". |
| LOZENGE | A solid preparation containing one or more medicaments, usually in a flavored, sweetened base which is intended to dissolve or disintegrate slowly in the mouth. A lollipop is a lozenge on a stick. |
| MOUTHWASH | An aqueous solution which is most often used for its deodorant, refreshing, or antiseptic effect. |
| OIL | An unctuous, combustible substance which is liquid, or easily liquefiable, on warming, and is soluble in ether but insoluble in water. Such substances, depending on their origin, are classified as animal, mineral, or vegetable oils. |
| OINTMENT | A semisolid[3] dosage form, usually containing <20% water and volatiles[5] and >50% hydrocarbons, waxes, or polyols as the vehicle. This dosage form is generally for external application to the skin or mucous membranes. |
| OINTMENT, AUGMENTED | An ointment dosage form that enhances drug delivery. Augmentation does not refer to the strength of the drug in the dosage form. NOTE: CDER has decided to refrain from expanding the use of this dosage form due to difficulties in setting specific criteria that must be met to be considered "augmented". |
| PASTE | A semisolid[3] dosage form, containing a large proportion (20-50%) of solids finely dispersed in a fatty vehicle. This dosage form is generally for external application to the skin or mucous membranes. |
| PASTILLE | An aromatic preparation, often with a pleasing flavor, usually intended to dissolve in the mouth. |
| PATCH | A drug delivery system that often contains an adhesive backing that is usually applied to an external site on the body. Its ingredients either passively diffuse from, or are actively transported from, some portion of the patch. Depending upon the patch, the ingredients are either delivered to the outer surface of the body or into the body. A patch is sometimes synonymous with the terms 'extended release film' and 'system'. |
| PATCH, EXTENDED RELEASE | A drug delivery system in the form of a patch that releases the drug in such a manner that a reduction in dosing frequency compared to that drug presented as a conventional dosage form (e.g., a solution or a prompt drug-releasing, conventional solid dosage form). |
| PATCH, EXTENDED RELEASE, ELECTRICALLY CONTROLLED | A drug delivery system in the form of a patch which is controlled by an electric current that releases the drug in such a manner that a reduction in dosing frequency compared to that drug presented as a conventional dosage form (e.g., a solution or a prompt drug-releasing, conventional solid dosage form). |
| PELLET | A small sterile solid mass consisting of a highly purified drug (with or without excipients) made by the formation of granules, or by compression and molding. |
| PELLETS, COATED, EXTENDED RELEASE | A solid dosage form in which the drug itself is in the form of granules to which varying amounts of coating have been applied, and which releases a drug (or drugs) in such a manner to allow a reduction in dosing frequency as compared to that drug (or drugs) presented as a conventional dosage form. |
| PILL | A small, round solid dosage form containing a medicinal agent intended for oral administration. |
| PLASTER | Substance intended for external application made of such materials and of such consistency as to adhere to the skin and attach to a dressing; plasters are intended to afford protection and support and/or to furnish an occlusion and macerating action and to bring medication into close contact with the skin. |
| POULTICE | A soft, moist mass of meal, herbs, seed, etc., usually applied hot in cloth that consists of gruel-like consistency. |
| POWDER | An intimate mixture of dry, finely divided drugs and/or chemicals that may be intended for internal or external use. |
| POWDER, FOR SOLUTION | An intimate mixture of dry, finely divided drugs and/or chemicals, which, upon the addition of suitable vehicles, yields a solution. |
| POWDER, FOR SUSPENSION | An intimate mixture of dry, finely divided drugs and/or chemicals, which, upon the addition of suitable vehicles, yields a suspension (a liquid preparation containing the solid particles dispersed in the liquid vehicle). |
| SALVE | A thick ointment or cerate (a fat or wax based preparation with a consistency between an ointment and a plaster). |

TABLE 10-1-continued

Dosage forms

| NAME | DEFINITION |
|---|---|
| SOLUTION | A clear, homogeneous liquid[1] dosage form that contains one or more chemical substances dissolved in a solvent or mixture of mutually miscible solvents. |
| SOLUTION, CONCENTRATE | A liquid preparation (i.e., a substance that flows readily in its natural state) that contains a drug dissolved in a suitable solvent or mixture of mutually miscible solvents; the drug has been strengthened by the evaporation of its nonactive parts. |
| SOLUTION, FOR SLUSH | A solution for the preparation of an iced saline slush, which is administered by irrigation and used to induce regional hypothermia (in conditions such as certain open heart and kidney surgical procedures) by its direct application. |
| SOLUTION, GEL FORMING/DROPS | A solution, which after usually being administered in a drop-wise fashion, forms a gel. |
| SOLUTION, GEL FORMING, EXTENDED RELEASE | A solution that forms a gel when it comes in contact with ocular fluid, and which allows at least a reduction in dosing frequency. |
| SOLUTION/DROPS | A solution which is usually administered in a drop-wise fashion. |
| SUPPOSITORY | A solid body of various weights and shapes, adapted for introduction into the rectal orifice of the human body; they usually melt, soften, or dissolve at body temperature. |
| SUPPOSITORY, EXTENDED RELEASE | A drug delivery system in the form of a suppository that allows for a reduction in dosing frequency. |
| SUSPENSION | A liquid1 dosage form that contains solid particles dispersed in a liquid vehicle. |
| SUSPENSION, EXTENDED RELEASE | A liquid preparation consisting of solid particles dispersed throughout a liquid phase in which the particles are not soluble; the suspension has been formulated in a manner to allow at least a reduction in dosing frequency as compared to that drug presented as a conventional dosage form (e.g., as a solution or a prompt drug-releasing, conventional solid dosage form). |
| SUSPENSION/DROPS | A suspension which is usually administered in a dropwise fashion. |
| SYRUP | An oral solution containing high concentrations of sucrose or other sugars; the term has also been used to include any other liquid dosage form prepared in a sweet and viscid vehicle, including oral suspensions. |
| TABLET | A solid dosage form containing medicinal substances with or without suitable diluents. |
| TABLET, CHEWABLE | A solid dosage form containing medicinal substances with or without suitable diluents that is intended to be chewed, producing a pleasant tasting residue in the oral cavity that is easily swallowed and does not leave a bitter or unpleasant after-taste. |
| TABLET, COATED | A solid dosage form that contains medicinal substances with or without suitable diluents and is covered with a designated coating. |
| TABLET, COATED PARTICLES | A solid dosage form containing a conglomerate of medicinal particles that have each been covered with a coating. |
| TABLET, DELAYED RELEASE | A solid dosage form which releases a drug (or drugs) at a time other than promptly after administration. Enteric-coated articles are delayed release dosage forms. |
| TABLET, DELAYED RELEASE PARTICLES | A solid dosage form containing a conglomerate of medicinal particles that have been covered with a coating which releases a drug (or drugs) at a time other than promptly after administration. Enteric-coated articles are delayed release dosage forms. |
| TABLET, DISPERSIBLE | A tablet that, prior to administration, is intended to be placed in liquid, where its contents will be distributed evenly throughout that liquid. Note: The term 'tablet, dispersible' is no longer used for approved drug products, and it has been replaced by the term 'tablet, for suspension'. |
| TABLET, EFFERVESCENT | A solid dosage form containing mixtures of acids (e.g., citric acid, tartaric acid) and sodium bicarbonate, which release carbon dioxide when dissolved in water; it is intended to be dissolved or dispersed in water before administration. |
| TABLET, EXTENDED RELEASE | A solid dosage form containing a drug which allows at least a reduction in dosing frequency as compared to that drug presented in conventional dosage form. |
| TABLET, FILM COATED | A solid dosage form that contains medicinal substances with or without suitable diluents and is coated with a thin layer of a water-insoluble or water-soluble polymer. |
| TABLET, FILM COATED, EXTENDED RELEASE | A solid dosage form that contains medicinal substances with or without suitable diluents and is coated with a thin layer of a water-insoluble or water-soluble polymer; the tablet is formulated in such manner as to make the contained medicament available over an extended period of time following ingestion. |
| TABLET, FOR SOLUTION | A tablet that forms a solution when placed in a liquid. |
| TABLET, FOR SUSPENSION | A tablet that forms a suspension when placed in a liquid (formerly referred to as a 'dispersible tablet'). |
| TABLET, MULTILAYER | A solid dosage form containing medicinal substances that have been compressed to form a multiple-layered tablet or a tablet-within-a-tablet, the inner tablet being the core and the outer portion being the shell. |
| TABLET, MULTILAYER, EXTENDED RELEASE | A solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form. |
| TABLET, ORALLY DISINTEGRATING | A solid dosage form containing medicinal substances which disintegrates rapidly, usually within a matter of seconds, when placed upon the tongue. |
| TABLET, ORALLY DIS-INTEGRATING, DELAYED RELEASE | A solid dosage form containing medicinal substances which disintegrates rapidly, usually within a matter of seconds, when placed upon the tongue, but which releases a drug (or drugs) at a time other than promptly after administration. |
| TABLET, SOLUBLE | A solid dosage form that contains medicinal substances with or without suitable diluents and possesses the ability to dissolve in fluids. |
| TABLET, SUGAR COATED | A solid dosage form that contains medicinal substances with or without suitable diluents and is coated with a colored or an uncolored water-soluble sugar. |

Footnotes:
[1] A liquid is pourable; it flows and conforms to its container at room temperature. It displays Newtonian or pseudoplastic flow behavior.
[2] Previously the definition of a lotion was "The term lotion has been used to categorize many topical suspensions, solutions, and emulsions intended for application to the skin." The current definition of a lotion is restricted to an emulsion.
[3] A semisolid is not pourable; it does not flow or conform to its container at room temperature. It does not flow at low shear stress and generally exhibits plastic flow behavior.
[4] A colloidal dispersion is a system in which particles of colloidal dimension (i.e., typically between 1 nm and 1 μm) are distributed uniformly throughout a liquid.
[5] Percent water and volatiles are measured by a loss on drying test in which the sample is heated at 105° C. until constant weight is achieved.

EXAMPLE 11

Route of administration. A suitable route of administration for a dosage form containing a pharmaceutically active compound of the present invention may be chosen from among those listed in Table 11-1.

TABLE 11-1

| Routes of administration | |
|---|---|
| NAME | DEFINITION |
| BUCCAL | Administration directed toward the cheek, generally from within the mouth. |
| CONJUNCTIVAL | Administration to the conjunctiva, the delicate membrane that lines the eyelids and covers the exposed surface of the eyeball. |
| CUTANEOUS | Administration to the skin. |
| ENDOSINUSIAL | Administration within the nasal sinuses of the head. |
| ENTERAL | Administration directly into the intestines. |
| EPIDURAL | Administration upon or over the dura mater. |
| EXTRACORPOREAL | Administration outside of the body. |
| HEMODIALYSIS | Administration through hemodialysate fluid. |
| INFILTRATION | Administration that results in substances passing into tissue spaces or into cells. |
| INTERSTITIAL | Administration to or in the interstices of a tissue. |
| INTRA-ABDOMINAL | Administration within the abdomen. |
| INTRA-ARTERIAL | Administration within an artery or arteries. |
| INTRA-ARTICULAR | Administration within a joint. |
| INTRACARTILAGINOUS | Administration within a cartilage; endochondral. |
| INTRACAUDAL | Administration within the cauda equina. |
| INTRACORONARY | Administration within the coronary arteries. |
| INTRADERMAL | Administration within the dermis. |
| INTRADUCTAL | Administration within the duct of a gland. |
| INTRADUODENAL | Administration within the duodenum. |
| INTRADURAL | Administration within or beneath the dura. |
| INTRAEPIDERMAL | Administration within the epidermis. |
| INTRAESOPHAGEAL | Administration within the esophagus. |
| INTRAGASTRIC | Administration within the stomach. |
| INTRAGINGIVAL | Administration within the gingivae. |
| INTRALYMPHATIC | Administration within the lymph. |
| INTRAMEDULLARY | Administration within the marrow cavity of a bone. |
| INTRAMENINGEAL | Administration within the meninges (the three membranes that envelope the brain and spinal cord). |
| INTRAMUSCULAR | Administration within a muscle. |
| INTRAOCULAR | Administration within the eye. |
| INTRAOVARIAN | Administration within the ovary. |
| INTRAPERICARDIAL | Administration within the pericardium. |
| INTRAPERITONEAL | Administration within the peritoneal cavity. |
| INTRAPLEURAL | Administration within the pleura. |
| INTRAPULMONARY | Administration within the lungs or its bronchi. |
| INTRASINAL | Administration within the nasal or periorbital sinuses. |
| INTRASPINAL | Administration within the vertebral column. |
| INTRASYNOVIAL | Administration within the synovial cavity of a joint. |
| INTRATENDINOUS | Administration within a tendon. |
| INTRATHECAL | Administration within the cerebrospinal fluid at any level of the cerebrospinal axis, including injection into the cerebral ventricles. |
| INTRATHORACIC | Administration within the thorax (internal to the ribs); synonymous with the term endothoracic. |
| INTRATUMOR | Administration within a tumor. |
| INTRAUTERINE | Administration within the uterus. |
| INTRAVASCULAR | Administration within a vessel or vessels. |
| INTRAVENOUS | Administration within or into a vein or veins. |
| INTRAVENOUS BOLUS | Administration within or into a vein or veins all at once. |
| INTRAVENOUS DRIP | Administration within or into a vein or veins over a sustained period of time. |
| INTRAVENTRICULAR | Administration within a ventricle. |
| INTRAVESICAL | Administration within the bladder. |

TABLE 11-1-continued

| Routes of administration | |
|---|---|
| NAME | DEFINITION |
| INTRAVITREAL | Administration within the vitreous body of the eye. |
| NASAL | Administration to the nose; administered by way of the nose. |
| OPHTHALMIC | Administration to the external eye. |
| ORAL | Administration to or by way of the mouth. |
| OROPHARYNGEAL | Administration directly to the mouth and pharynx. |
| OTHER | Administration is different from others on this list. |
| PARENTERAL | Administration by injection, infusion, or implantation. |
| PERCUTANEOUS | Administration through the skin. |
| PERIARTICULAR | Administration around a joint. |
| PERIDURAL | Administration to the outside of the dura mater of the spinal cord.. |
| PERINEURAL | Administration surrounding a nerve or nerves. |
| PERIODONTAL | Administration around a tooth. |
| RECTAL | Administration to the rectum. |
| RESPIRATORY (INHALATION) | Administration within the respiratory tract by inhaling orally or nasally for local or systemic effect. |
| SOFT TISSUE | Administration into any soft tissue. |
| SUBCONJUNCTIVAL | Administration beneath the conjunctiva. |
| SUBCUTANEOUS | Administration beneath the skin; hypodermic. Synonymous with the term SUBDERMAL. |
| SUBLINGUAL | Administration beneath the tongue. |
| SUBMUCOSAL | Administration beneath the mucous membrane. |
| TOPICAL | Administration to a particular spot on the outer surface of the body. The E2B term TRANSMAMMARY is a subset of the term TOPICAL. |
| TRANSDERMAL | Administration through the dermal layer of the skin to the systemic circulation by diffusion. |
| TRANSMUCOSAL | Administration across the mucosa. |

The foregoing description of the preferred embodiments of the present invention have been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed:

1. A method of supplementing a diet of a mammal, comprising:
  administering to said mammal a pharmaceutically effective amount of a compound having a chemical formula:

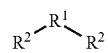

where R¹=

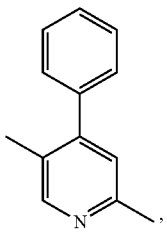

and
where R²=

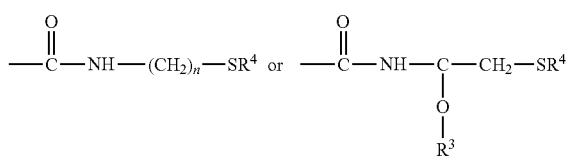

where R³=ethyl or methyl, R⁴=hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4.

2. The method of claim 1, including using oral administration.

3. The method of claim 1, including administering between about 0.5 and about 40 milligrams of said compound per kilogram of said mammal's total body weight per day.

4. The method of claim 1, including using transdermal administration.

5. The method of claim 1, including using nasal administration.

6. The method of claim 1, including using administration by suppository.

7. The method of claim 1, including using intravenous administration.

8. The method of claim 1, including administering said compound with another antioxidant.

9. The method of claim 1. including selecting said antioxidant from a list of antioxidants consisting of vitamin-E, vitamin-D, cysteine, glutathione, lipoic acid and combinations thereof.

10. A method to remove heavy metals and toxins from a mammal, comprising:
administering to said mammal a pharmaceutically effective amount of a compound having a chemical formula:

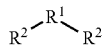

where R¹=

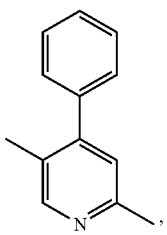

where R²=

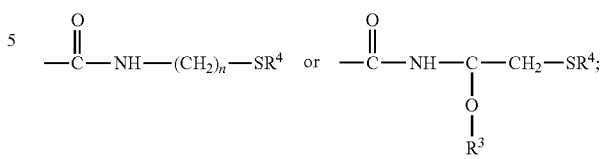

or
and
where R³=ethyl or methyl, R⁴=hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4.

11. The method of claim 10, including using oral administration.

12. The method of claim 10, including administering between about 0.5 and about 40 milligrams of said compound per kilogram of said mammal's total body weight per day.

13. The method of claim 10, including using transdermal administration.

14. The method of claim 10, including using nasal administration.

15. The method of claim 10, including using administration by suppository.

16. The method of claim 10, including using intravenous administration.

17. The method of claim 10, including administering said compound with a water soluble metal chelator.

18. The method of claim 17, including selecting said water soluble metal chelator from a group consisting of glutathione (GSH), dihydrolipoic acid (DLPA), lipoic acid (LPA), N-acetylcysteine (NAC), dimercaptopropane sultanate (DMPS), dimercaptosuccinic acid (DMSA), ethylenediaminetetraacetie acid (EDTA) and mixtures thereof.

19. A method of relieving oxidative stress in a mammal, comprising:
administering to said mammal a pharmaceutically effective amount of a compound having a chemical formula:

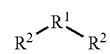

where R¹=

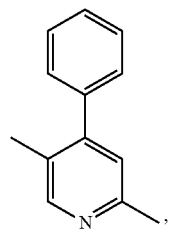

where R² =

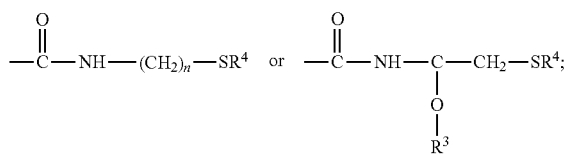

and where R³=ethyl or methyl, R⁴=hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4.

20. The method of claim 19, including using oral administration.

21. The method of claim 19, including administering between about 0.5 and about 100 milligrams of said compound per kilogram of said mammal's total body weight per day.

22. The method of claim 19, including using transdermal administration.

23. The method of claim 19, including using nasal administration.

24. The method of claim 19, including using administration by suppository.

25. The method of claim 19, including using intravenous administration.

26. The method of claim 19, including administering said compound with a precursor of glutathione, 27. The method of claim 26, including selecting said precursor of glutathione from a group consisting of cysteine, N-acetylcysteine, glycine, glutamate and combinations thereof.

28. The method of claim 19, including administering said compound with a dietary supplement that supports glutathione synthesis.

29. The method of claim 28, including selecting said dietary supplement from a group consisting of whey protein, N-acetylcysteine, cysteine, glutathione, nicotine adenine dinucleotide (NAD⁺), reduced nicotine adenine dinucleotide (NADH), glycylcysteine (gly-cys), glutamylcysteine (glu-cys), and combinations thereof.

30. A pharmaceutical composition, comprising:
a pharmaceutically effective amount of a compound having a chemical formula:

where R¹=

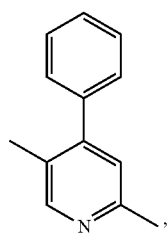

where R² =

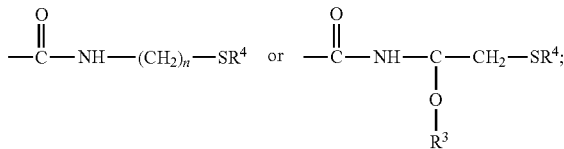

and where R³=ethyl or methyl, R⁴ hydrogen, glutathione, cysteine, alphadihydrolipoie acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4; and a pharmaceutically acceptable excipient.

31. The composition of claim 30, wherein said excipient is selected from a group of materials consisting of Acacia, Acesulfame Potassium, Acetic Acid, Acetone, Acetyltributyl Citrate, Acetyltriethyl Citrate, Agar, Albumin, Alcohol, Alginic Acid, Aliphatic Polyesters, Alitame, Almond Oil, Alpha Tocopherol, Aluminum Hydroxide Adjuvant, Aluminum Oxide, Aluminum Phosphate Adjuvant, Aluminum Stearate, Ammonia Solution, Ammonium Alginate, Ascorbic Acid, Ascorbyl Palmitate, Aspartame, Attapulgite, Bentonite, Benzalkonium Chloride, Benzethonium Chloride, Benzoic Acid, Benzyl Alcohol, Benzyl Benzoate, Boric Acid, Bronopol, Butylated Hydroxyanisole, Butylated Hydroxytoluene, Butylparaben, Calcium Alginate, Calcium Carbonate, Calcium Phosphate, Dibasic Anhydrous, Calcium Phosphate, Dibasic Dihydrate, Calcium Phosphate, Tribasic, Calcium Stearate, Calcium Sulfate, Canola Oil, Carbomer, Carbon Dioxide, Carboxymethylcellulose Calcium, Carboxymethylcellulose Sodium, Carrageenan, Castor Oil, Hydrogenated Castor Oil, Cellulose, Microcrystalline, Cellulose, Powdered, Cellulose, Silicified Microcrystalline, Cellulose Acetate, Cellulose Acetate Phthalate, Ceratonia, Cetostearyl Alcohol, Cetrimide, Cetyl Alcohol, Cetylpyridinium Chloride, Chitosan, Chlorhexidine, Chlorobutanol, Chlorocresol, Chlorodifluoroethane (HCFC), Chlorofluorocarbons (CFC), Chloroxylenol, Cholesterol, Citric Acid Monohydrate, Colloidal, Silicon Dioxide, Coloring Agents, Copovidone, Corn Oil, Cottonseed Oil, Cresol, Croscarmellose Sodium, Crospovidone, Cyclodextrins, Cyclomethicone, Denatonium Benzoate, Dextrates, Dextrin, Dextrose, Dibutyl Phthalate, Dibutyl Sebacate, Diethanolamine, Diethyl Phthalate, Difluoroethane (HFC), Dimethicone, Dimethyl Ether, Dimethyl Phthalate, Dimethyl Sulfoxide, Dimethylacetamide, Disodium Edetate, Docusate Sodium, Edetic Acid, Erythorbic Acid, Erythritol, Ethyl Acetate, Ethyl Lactate, Ethyl Maltol, Ethyl Oleate, Ethyl Vanillin, Ethylcellulose, Ethylene Glycol Palmitostearate, Ethylene Vinyl Acetate, Ethylparaben, Fructose, Fumaric Acid, Gelatin, Glucose, Glycerin, Glyceryl Behenate, Glyceryl Monooleate, Glyceryl Monostearate, Glyceryl Palmitostearate, Glycofurol, Guar Gum, Hectorite, Heptafluoropropane (HFC), Hexetidine, Hydrocarbons (HC), Hydrochloric Acid, Hydroxyethyl Cellulose, Hydroxyethylmethyl Cellulose, Hydroxypropyl Cellulose, Hydroxypropyl Cellulose, Low-substituted, Hydroxypropyl Starch, Hypromellose, Hypromellose Acetate Succinate, Hypromellose Phthalate, Imidurea, Inulin, Iron Oxides, Isopropyl Alcohol, Isopropyl Myristate, Isopropyl Palmitate, Kaolin, Lactic Acid, Lactitol, Lactose Anhydrous, Lactose Monohydrate, Lactose Spray-Dried, Lanolin, Lanolin Hydrous, Lanolin Alcohols, Lauric Acid, Lecithin, Leucine, Linoleic Acid, Macrogol 15 Hydroxystearate, Magnesium Aluminum Silicate, Magnesium Carbonate, Magnesium Oxide, Magnesium Silicate, Magnesium Stearate, Magnesium Trisilicate, Malic Acid, Maltitol, Maltitol Solution, Maltodextrin, Maltol, Maltose, Mannitol, Mediumchain Triglycerides, Meglumine, Menthol, Methylcellulose, Methylparaben, Mineral Oil, Mineral Oil, Light, Mineral Oil and Lanolin Alcohols, Monoethanolamine, Monosodium Glutamate, Monothioglycerol, Myristic Acid, Neohesperidin Dihydrochalcone, Nitrogen, Nitrous Oxide, Octyldodecanol, Oleic Acid, Oleyl Alcohol, Olive Oil, Palmitic Acid, Paraffin, Peanut Oil, Pectin, Petrolatum and Lanolin Alcohols, Petrolatum, Phenol, Phenoxyethanol, Phenylethyl Alcohol, Phenylmercuric Acetate, Phenylmercuric Borate, Phenylmercuric Nitrate, Phosphoric Acid, Polacrilin Potassium, Poloxamer, Polycarbophil, Polydextrose, Polyethylene Glycol, Polyethylene Oxide, Polymethacrylates, Poly(methyl vinyl ether/maleic anhydride), Polyoxyethylene Alkyl Ethers, Polyoxyethylene Castor Oil Derivatives, Polyoxyethylene Sorbitan Fatty Acid Esters, Polyoxyethylene Stearates, Polyvinyl Acetate, Phthalate, Polyvinyl Alcohol, Potassium Alginate, Potassium Benzoate, Potassium Bicarbonate, Potassium Chloride, Potassium Citrate, Potassium Hydroxide, Potassium Metabisulfite, Potassium Sorbate, Povidone, Propionic Acid, Propyl Gallate, Propylene Carbonate, Propylene Glycol, Propylene Glycol Alginate, Propylparaben, 2-Pyrrolidone, Raffinose, Saccharin, Saccharin Sodium, Saponite, Sesame Oil, Simethicone, Sodium Acetate, Sodium Alginate, Sodium Ascorbate, Sodium Benzoate, Sodium Bicarbonate, Sodium Borate, Sodium Chloride, Sodium Citrate Dihydrate, Sodium Cyclamate, Sodium Hyaluronate, Sodium Hydroxide, Sodium Lactate, Sodium Lauryl Sulfate, Sodium Metabisulfite, Sodium Phosphate, Dibasic, Sodium Phosphate, Monobasic, Sodium Propionate, Sodium Starch Glycolate, Sodium Stearyl Fumarate, Sodium Sulfite, Sorbic Acid, Sorbitan Fatty Acid Esters, Sorbitol, Soybean Oil, Starch, Starch, Pregelatinized, Starch, Sterilizable Maize, Stearic Acid, Stearyl Alcohol, Sucralose, Sucrose, Sugar, Compressible Sugar, Confectioner's Sugar, Sulfobutylether β-Cyclodextrin, Sulfuric Acid, Sunflower Oil, Suppository Bases, Hard Fat, Talc, Tartaric Acid, Tetrafluoroethane (HFC), Thaumatin, Thymol, Titanium Dioxide, Tragacanth, Trehalose, Triacetin, Tributyl Citrate, Triethanolamine, Triethyl Citrate, Vanillin, Hydrogenated Vegetable Oil, Water, Wax, Anionic Emulsifying, Wax, Carnauba, Wax, Cetyl Esters, Microcrystalline Wax, Nonionic Emulsifying Wax, White Wax, Yellow Wax, Xanthan Gum, Xylitol, Zein, Zinc Acetate, Zinc Stearate and combinations thereof.

32. The composition of claim 30, wherein said excipient is selected from a group of materials consisting of albumin, almond oil, ascorbic acid, benzoic acid, calcium stearate, canola oil, calcium carboxymethylcellulose, sodium carboxymethylellulose, castor oil, hydrogenated castor oil, microcrystalline cellulose, corn oil, cotton seed oil, cyclodextrins, ethylene glycol palmitostearate, gelatin, glycerin, hydroxyethyl cellulose, hydroxyethylmethyl cellulose, hydroxypropyl cellulose, low-substituted hydroxypropyl cellulose, lanolin, linoleic acid, magnesium silicate, magnesium stearate, medium-chain triglycerides, mineral oil, olive oil, peanut oil, pectin, compressible sugar, sunflower oil, hydrogenate vegetable oil, water and combinations thereof.

33. The composition of claim 30, further including an additional antioxidant.

34. The composition of claim 33, wherein said additional antioxidant is selected from a group consisting of vitamin-E, vitamin-D, cystine, glutathione, lipoic acid and combinations thereof.

35. The composition of claim 30, further including a water soluble metal chelator.

36. The composition of claim 35, wherein said water soluble metal chelator is selected from a group consisting of glutathione (GSH), dihydrolipoic acid (DLPA), lipoic acid (LPA), N-acetylcysteine (NAC), dimercaptopropane sulfonate (DMPS), dimercaptosuccinic acid (DMSA), ethylenediaminetetraacetic acid (EDTA), and mixtures thereof.

37. The composition of claim 30, further including a precursor of glutathione.

38. The composition of claim 37, wherein said precursor of glutathione is selected from a group of materials consisting of cysteine, N-acetylcystein, glycine, glutamate and combinations thereof.

39. The composition of claim 30, further including an additional dietary supplement that supports glutathione synthesis.

40. The composition of claim 39, wherein said additional dietary supplement is selected from a group of materials consisting of whey protein, N-acetylcysteine, cysteine, glutathione, nicotine adenine dinucleotide (NAD$^+$), reduced nicotine adenine dinucleotide (NADH), glycylcysteine (glycys), glutamylcysteine (glucyc), and combinations thereof.

41. The composition of claim 30, further including a material selected from a group consisting of a binder, a preservative, a mineral supplement, a bulking agent, a flavoring agent and combinations thereof.

42. The composition of claim 30, including between about 99.5 and about 85 weight percent active compound and between about 0.5 and about 15 weight percent excipient.

43. A pharmaceutical composition, comprising:
between about 99.5 and about 5 weight percent of a pharmaceutically effective amount of a compound having a chemical formula:

where $R^1 =$

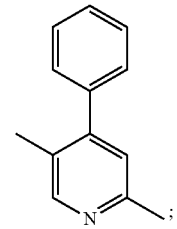

and
where $R^2 =$

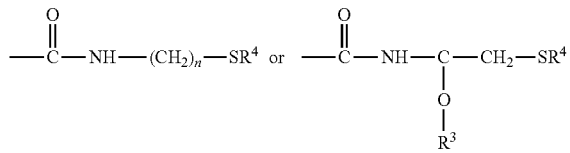

where $R^3$=ethyl or methyl, $R^4$=hydrogen, glutathione, cysteine, alphadihydrolipoic acid, cystamine, thiolphosphate, 5'thioladenosine, L-homocysteine, co-enzyme A, 2-mercaptoethanol, dithiothreitol, iodoacetate, bromoacetate, fluoroacetate or chloroacetate and n=2-4;
between about 0.0 and about 50 weight percent of an additional antioxidant;
between about 0.0 and about 20 weight percent of a water soluble metal chelator;
between about 0.0 and about 50 weight percent of glutathione;
between about 0.0 and about 50 weight percent of an additional dietary supplement that supports glutathione synthesis; and between about 0.5 and about 50 weight percent of a pharmaceutically acceptable excipient.
44. The composition of claim 43 wherein said compound has a chemical formula
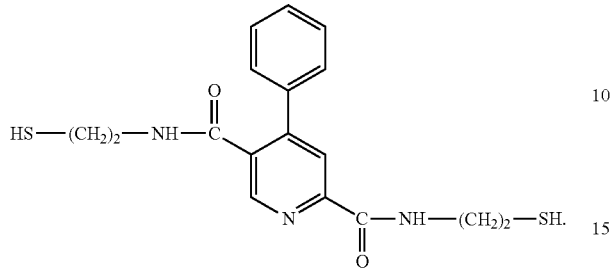
45. The composition of claim 29 wherein said compound has a chemical formula
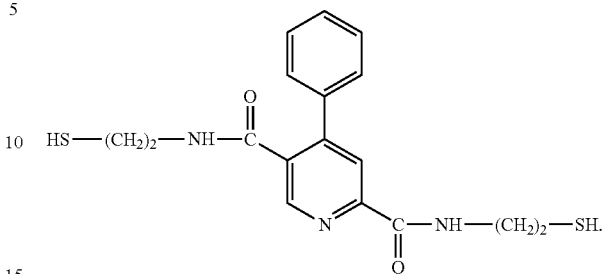
* * * * *